US009302257B2

(12) United States Patent
Müller et al.

(10) Patent No.: US 9,302,257 B2
(45) Date of Patent: Apr. 5, 2016

(54) PROCESS FOR THE PREPARATION OF A TITANIUM ZEOLITE CATALYST

(75) Inventors: Ulrich Müller, Neustadt (DE); Peter Rudolf, Ladenburg (DE); Georg Krug, Moerlenbach (DE); Rainer Senk, Ludwigshafen (DE)

(73) Assignees: BASF SE, Ludwigshafen (DE); The Dow Chemical Company, Midland, MI (US)

( * ) Notice: Subject to any disclaimer, the term of this patent is extended or adjusted under 35 U.S.C. 154(b) by 1057 days.

(21) Appl. No.: 12/954,802

(22) Filed: Nov. 26, 2010

(65) Prior Publication Data

US 2011/0130579 A1    Jun. 2, 2011

Related U.S. Application Data

(60) Provisional application No. 61/264,737, filed on Nov. 27, 2009.

(51) Int. Cl.

| B01J 29/04 | (2006.01) |
| B01J 29/89 | (2006.01) |
| B01J 37/00 | (2006.01) |
| B01J 37/08 | (2006.01) |
| C07D 301/12 | (2006.01) |

(52) U.S. Cl.
CPC ............. *B01J 29/89* (2013.01); *B01J 37/0018* (2013.01); *B01J 37/084* (2013.01); *C07D 301/12* (2013.01); *B01J 2229/42* (2013.01)

(58) Field of Classification Search
None
See application file for complete search history.

(56) References Cited

U.S. PATENT DOCUMENTS

| 4,001,346 A | | 1/1977 | Chu | |
| 4,638,106 A | * | 1/1987 | Pieters et al. | 585/640 |
| 4,798,816 A | | 1/1989 | Ratcliffe et al. | |
| 5,397,475 A | | 3/1995 | Millar et al. | |
| 5,932,187 A | | 8/1999 | Ledon et al. | |
| 6,740,764 B1 | * | 5/2004 | Chen et al. | 549/533 |
| 2003/0162983 A1 | | 8/2003 | Strebelle et al. | |
| 2004/0167342 A1 | * | 8/2004 | Strebelle et al. | 549/533 |
| 2005/0054864 A1 | | 3/2005 | Strebelle et al. | |
| 2007/0149790 A1 | | 6/2007 | Strebelle et al. | |

FOREIGN PATENT DOCUMENTS

| DE | 42 22 109 A1 | 1/1994 |
| EP | 0 272 830 B1 | 6/1988 |
| EP | 1 122 249 A1 | 8/2001 |
| RU | 2 256 613 | 7/2005 |
| RU | 2 332 409 | 8/2008 |
| WO | WO 01/41926 A1 | 6/2001 |
| WO | WO 02/28774 A2 | 4/2002 |
| WO | WO 02/28774 A3 | 4/2002 |

OTHER PUBLICATIONS

Akata et al., "Titanosilicate ETS-10 as a Lewis acid catalyst in the Meerwein-Ponndorf-Verley (MPV) reaction", J Porous Mater (2008) 15:351-357.*
Zhang et al., "Coke deposition and characterization on titanium silicalite-1 catalyst in cyclohexanone ammoximation", Applied Catalysis A: General 307 (2006) 222-230.*
"Ullmann's Ezyklopädie der Technischen Chemie" 4$^{th}$ edition, vol. 2, 1972, p. 295.
"Ullmann's Encyclopedia of Industrial Chemistry", 5$^{th}$ edition, High-Performance Fibers to Imidazole and Derivatives, vol. 13, 1989 pp. 447-457.
"Ullmann's Encyclopedia of Industrial Chemistry", 5$^{th}$ edition, High-Performance Fibers to Imidazole and Derivatives, vol. 13, 1989 pp. 447-456.
International Search Report issued Jan. 25, 2011, in PCT /EP2010/ 067987 filed Nov. 23, 2010.
Office Action dated Mar. 27, 2015 in Mexican Application No. MX/a/ 2012/005845 with English Translation.
Russian decision on grant of corresponding Russian Patent and English Translation issued in RU Application No. 2012126602 dated Mar. 30, 2015.
Akata, B., et al., "Titanosilicate ETS-10 as a Lewis Acid Catalyst in the Meerwein-Ponndorf-Verley (MPV) Reaction," *J. Porous Mater*, vol. 15, 2008, p. 351-357.
Zhang, X. et al., "Coke Deposition and Characterization on Titanium Silicalite-1 Catalyst in Cyclohexanone Ammoximation," *Applied Catalysis A: General*, vol. 307, 2006, p. 222-230.

* cited by examiner

*Primary Examiner* — Jennifer A Smith
*Assistant Examiner* — Anita Nassiri Motlagh
(74) *Attorney, Agent, or Firm* — Oblon, McClelland, Maier & Neustadt, L.L.P.

(57) ABSTRACT

A process for the preparation of a catalyst for the use in a hydrocarbon conversion reaction, said catalyst containing a titanium zeolite and carbonaceous material, the catalyst containing said carbonaceous material in an amount of from 0.01 to 0.5% by weight based on the total weight of titanium zeolite contained in the catalyst, the process comprising (i) preparing a catalyst containing the titanium zeolite and (ii) depositing carbonaceous material on the catalyst according to (i) in an amount of from 0.01 to 0.5% by weight based on the total weight of titanium zeolite contained in the catalyst by contacting said catalyst, prior to using the catalyst in said hydrocarbon conversion reaction, with a fluid containing at least one hydrocarbon in an inert atmosphere, to obtain the carbonaceous material containing catalyst, wherein in (ii), the catalyst is not contacted with an oxygen containing gas.

31 Claims, No Drawings

US 9,302,257 B2

PROCESS FOR THE PREPARATION OF A TITANIUM ZEOLITE CATALYST

This invention relates to a process for the preparation of a catalyst for the use in a hydrocarbon conversion reaction, said catalyst containing a titanium zeolite and carbonaceous material, the catalyst containing said carbonaceous material in an amount of from 0.01 to 0.5% by weight based on the total weight of titanium zeolite contained in the catalyst, the process comprising
(i) preparing a catalyst containing the titanium zeolite;
(ii) depositing carbonaceous material on the catalyst according to (i) in an amount of from 0.01 to 0.5% by weight based on the total weight of titanium zeolite contained in the catalyst by contacting said catalyst, prior to using the catalyst in said hydrocarbon conversion reaction, with a fluid containing at least one hydrocarbon in an inert atmosphere, to obtain the carbonaceous material containing catalyst,
wherein in (ii), the catalyst is not contacted with an oxygen containing gas. Additionally, this invention relates to a catalyst obtainable by said process, the catalyst containing carbonaceous material in a range of from 0.01 to 0.5% per weight based on the total weight of the titanium zeolite. Furthermore, the invention relates to the use of said catalysts for the conversion, in particular for the oxidation, of a hydrocarbon. Further, the present invention relates to a process for the preparation of propylene oxide in the presence of a catalyst containing at least one titanium zeolite and carbonaceous material, the catalyst comprising said carbonaceous material in a range of from 0.01 to 0.5% by weight based on the total weight of titanium zeolite, the process comprising
(i) providing a catalyst containing the titanium zeolite;
(ii) depositing carbonaceous material on the catalyst according to (i) in the range of from 0.01 to 0.5% by weight based on the total weight of titanium zeolite contained in the catalyst by contacting said catalyst, prior to using the catalyst in said hydrocarbon conversion reaction, with a fluid containing at least one hydrocarbon in an inert atmosphere, to obtain the carbonaceous material containing catalyst,
(iii) contacting the catalyst obtained according to (ii) with a reaction mixture comprising propylene, hydroperoxide, and at least one solvent,
wherein in (ii), the catalyst is not contacted with an oxygen containing gas Catalysts for the use in hydrocarbon conversion processes which have been pretreated with a hydrocarbon prior to their use have been previously described.

A process for the preparation of a pre-coked catalyst has for example been described in U.S. Pat. No. 4,001,346, which discloses a process for modifying a catalyst comprising an alumosilicate zeolite having ZSM-5 structure by depositing thereon a coating of coke produced by the decomposition of hydrocarbons. The pretreating step according to U.S. Pat. No. 4,001,346 is a two stage procedure, wherein the a first stage, the catalyst is provided with a coke content between about 15 and about 75 weight %, which substantially deactivates the catalyst, and wherein in a second stage, the catalyst is exposed to an oxygen containing atmosphere at elevated temperature to reduce the coke content to the desired value. The pretreating may be accomplished by using the uncoked catalyst in the reaction of interest, that is the selective production of para-xylene by methylation of toluene, and then regenerating the catalyst by burning off the deposits in a stream of air.

Similarly, EP 0 272 830 B1 describes the activation of an alkylation catalyst by depositing carbonaceous material on the catalyst to suppress its alkylation activity, and subsequent removal of more than about 95 weight % of the carbonaceous material by treating the catalyst with a gaseous oxidizing agent at an elevated temperature. The catalyst subjected to the process according to EP 0 272 830 B1 can either be a fresh catalyst, i.e., one that has not previously been used in the reaction of interest or a deactivated or partially deactivated catalyst. Thus, again a two stage procedure is disclosed, wherein initially an excess of carbonaceous material is deposited on the catalyst, which necessitates the subsequent treatment with an oxidizing agent in order to obtain an active catalyst.

Likewise, an activation and regeneration of a catalyst has been described in WO 01/41926 A1, which describes a process wherein a hydrooxidation catalyst is activated by contacting the deactivated catalyst with ozone.

U.S. Pat. No. 4,638,106 describes a process for improving the catalyst life of an acidic alumosilicate catalyst or a gallium silicate catalyst employed in the conversion of alcohols (e.g. methanol) and their ether derivatives (e.g. dimethyl ether). U.S. Pat. No. 4,638,106 describes a two stage procedure, wherein initially a low amount of a coke precursor is deposited on the external surface of the zeolite and wherein the such obtained catalyst is subsequently heat treated in an inert atmosphere in order to convert the coke precursor to coke.

In view of this prior art, it was an object of the present invention to provide a process for the preparation of a catalyst having improved catalytic properties when used in a hydrocarbon conversion reaction. Additionally, it was an object of the present invention to provide the improved catalyst as such and the use of said catalyst for the conversion of a hydrocarbon, in particular for the epoxidation of propylene.

Surprisingly, it was found that an improved catalyst can be prepared by a specific pretreatment process wherein carbonaceous material is deposited on the catalyst prior to use of said catalyst in the hydrocarbon conversion reaction.

Accordingly, the present invention provides a process for the preparation of a catalyst for the use in a hydrocarbon conversion reaction, said catalyst containing a titanium zeolite and carbonaceous material, the catalyst containing said carbonaceous material in an amount of from 0.01 to 0.5% by weight based on the total weight of titanium zeolite contained in the catalyst, the process comprising
(i) preparing a catalyst containing the titanium zeolite;
(ii) depositing carbonaceous material on the catalyst according to (i) in an amount of from 0.01 to 0.5% by weight based on the total weight of titanium zeolite contained in the catalyst by contacting said catalyst, prior to using the catalyst in said hydrocarbon conversion reaction, with a fluid containing at least one hydrocarbon in an inert atmosphere, to obtain the carbonaceous material containing catalyst,
wherein in (ii), the catalyst is not contacted with an oxygen containing gas.

In contrast to the processes described in the prior art, in the process according to the invention, a titanium zeolite containing catalyst is pretreated with a fluid containing at least one hydrocarbon in an inert atmosphere so as to obtain a new catalyst. In said pretreating procedure, the carbonaceous material is deposited on the catalyst in a controlled manner. Thus, the catalyst is not initially deactivated by an excess of carbonaceous material. Instead, an active catalyst is directly obtained which contains a controlled amount of carbonaceous material deposited thereon. containing gas after the deposition step nor subjected to a thermal treatment as described in Further, the obtained catalyst is neither subjected to a treatment with an oxygen U.S. Pat. No. 4,638,106 after depositing the carbonaceous material. Surprisingly, it has been found that the catalyst prepared by the process according to the invention, when used in hydrocarbon conversion reactions, preferably oxidation reactions and even more preferably epoxidation reactions such as epoxidation of propylene, provides highly selective conversion while maintaining high activity.

According to step (i) of the process of the present invention, a catalyst containing a titanium zeolite is prepared. As far as the titanium zeolite is concerned, no specific restrictions exist with the proviso that the catalyst containing said titanium zeolite can be employed as catalyst for the desired hydrocarbon conversion process.

As far as the at least one titanium zeolite according to (i) is concerned, no limitations exist.

Titanium zeolites are zeolites which contain no aluminum and in which the Si(IV) in the silicate lattice is partly replaced by titanium as Ti(IV). These titanium zeolites, in particular those having a crystal structure of the MWW type, and possible ways of preparing them are described, for example, in WO 02/28774 A2, the respective content of which is incorporated into the context of the present invention by reference.

All suitable titanium zeolites and mixtures of two or more of these materials, for example, inter alia, mesoporous and/or microporous titanium zeolites are used. The term "mesopores" as used in the context of the present invention relates to pores having a pore size in the range of from 2 nm to 50 nm and the term "micropores" relates to a pore size smaller than 2 nm, determined according to DIN 66134.

In this context, titanium zeolites having pentasil structure may be mentioned. A plurality of these titanium zeolites can be found, for example, in W. M. Meier, D. H. Olson and Ch. Baerlocher in "Atlas of zeolite Structure Types", Elsevier, 4$^{th}$ edition, London 1996.

In particular, the present invention relates to a process, as described above, and a catalyst obtainable by said process, the catalyst containing at least one titanium zeolite, wherein the at least one titanium zeolite has a structural type that can be, via X-ray diffraction, assigned to the structure types of ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, SCO, CFI, SGF, CGS, CHA, CHI, CLO, CON, CZP, DAC, DDR, DFO, DFT, DOH, DON, EAB, EDI, EMT, EON, EPI, ERI, ESV, ETR, EUO, FAU, FER, FRA, GIS, GIU, GME, GON, GOO, HEU, IFR, IHW, ISV, ITE, ITH, ITW, IWR, IWW, JBW, KFI, LAU, LEV, LIO, LIT, LOS, LOV, LTA, LTL, LTN, MAR, MAZ, MEI, MEL, MEP, MER, MFI, MFS, MON, MOR, MOZ, MSO, MTF, MTN, MTT, MTW, MWW, NAB, NAT, NES, NON, NPO, NSI, OBW, OFF, OSI, OSO, OWE, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SOD, SOS, SSY, STF, STI, STT, TER, THO, TON, TSC, UEI, UFI, UOZ, USI, UTL, VET, VFI, VNI, VSV, WIE, WEN, YUG, ZON or a mixture of one or more thereof.

Titanium zeolites having the structure MFI, MEL, MWW, BEA or FER or a mixed structure of two or more thereof, as for example a mixed MFI/MEL-, MFI/MWW-, MFI/FER-, MFI/BEA-, MEL/MWW-, MEL/BEA, MEL/FER, MWW/BEA-, MWW/FER- or a MFI/MEL/MWW-structure, are preferred in the context of the present invention. Particularly preferable the at least one titanium zeolite is a zeolite having MFI or MWW or a mixed MFI/MWW-structure, more preferably a MFI structure.

Accordingly, the present invention also describes a process, wherein the catalyst contains at least one titanium zeolite having the structure MFI, MEL, MWW, BEA or FER or a mixed structure of two or more thereof, particularly preferably wherein the catalyst contains at least one titanium zeolite having MFI structure.

Titanium zeolites having MFI-structure can be identified by means of a specific x-ray diffraction pattern as well as by lattice vibration band in the infrared region at about 960 cm$^{-1}$. The titanium zeolites thus differ from alkali metal titanates as well as from crystalline and amorphous TiO$_2$-phases.

The at least one titanium zeolite can additionally contain elements selected from the group consisting of the groups IIA, IVA, VA, VIA, VIIA, VIIIB, IB, IIB, IIIB, IVB, and VB of the periodic table, such as, for example, aluminum, boron, zirconium, chromium, tin, zinc, gallium, germanium, vanadium, iron, niobium, cobalt, nickel, or mixtures of two or more of these elements. If the catalyst contains two or more titanium zeolites, for example five, four, three or two titanium zeolites, these titanium zeolites can contain the same or different additional elements or different mixtures of two or more of these elements. Most preferably, the titanium zeolite of the present invention essentially consists of Si, O, and Ti.

Furthermore, the invention relates to a catalyst comprising at least one titanium zeolite and carbonaceous material in a range of from 0.01 to 0.5% by weight, based on the total weight of the titanium zeolite contained in the catalyst, said catalyst being obtainable by a process as described above, wherein the at least one titanium zeolite, is a titanium zeolite having the structure MFI, MEL, MWW, BEA or FER or a mixed structure of two or more thereof.

The titanium zeolite contained in the catalyst according to (i) can in principle be prepared by any conceivable method. Typically, the synthesis of the at least one titanium zeolite according to the present invention is carried out in hydrothermal systems involving the combination of an active source of silicon oxide and a titanium source, such as titanium oxide, with at least one template compound capable of forming the desired titanium zeolite in an aqueous suspension, for example in a basic suspension. Typically, organic templates are employed. Preferably, the synthesis is carried out at elevated temperatures, for example temperatures in the range of from to 150 to 200° C., preferably from 160 to 180° C.

In principle, any suitable compound can be used as silicon oxide source. Typical sources of silicon oxide (SiO$_2$) include silicates, silica hydrogel, silicic acid, colloidal silica, fumed silica, tetraalkoxysilanes, silicon hydroxides, precipitated silica and clays. Both so-called "wet-process silicon dioxide" and so-called "dry-process" silicon dioxide can be employed. In these cases, the silicon dioxide is particularly preferably amorphous, wherein the size of the silicon dioxide particles is, for example, in the range of from 5 to 100 nm and the surface area of the silicon dioxide particles is, for example, in the range of from 50 to 500 m$^2$/g. Colloidal silicon dioxide is, inter alia, commercially available as Ludox®, Syton®, Nalco®, or Snowtex®. "Wet process" silicon dioxide is, inter alia, commercially available as Hi-Sil®, Ultrasil®, Vulcasil®, Santocel®, Valron-Estersil®, Tokusil® or Nipsil®. "Dry process" silicon dioxide is commercially available, inter alia, as Aerosil®, Reolosil®, Cab-O-Sil®, Fransil® or Arc-Silica®. It is as well within the scope of the present invention to use a silicon dioxide precursor compound as silicon oxide source. For example, tetraalkoxysilanes, such as for example, tetraethoxysilane or tetrapropoxysilane, may be mentioned as precursor compound.

As template, any template suitable to provide the desired zeolitic structure can be used. Preferably, organic compounds containing nitrogen or phosphorus, such as nitrogen-containing organic bases such as tertiary amines or quaternary ammonium compounds, such as for example salts of tetramethylammonium, tetraethylammonium, tetrapropylammonium, tetrabutylammonium, dibenzyldimethylammonium, dibenzyldiethylammonium, benzyltrimethylammonium and 2-(hydroxyalkyl)trialkyl-ammonium, where alkyl is methyl, or ethyl, or methyl and ethyl, are used as template for the preparation of the at least one titanium zeolite. Non-limiting examples of amines useful in the present process include trimethylamine, triethylamine, tripropylamine, ethylenediamine, propylenediamine, butenediamine, pentenediamine, propanediamine, butanediamine, pentanediamine, hexanediamine, methylamine, ethylamine, propylamine, butylamine, dimethylamine, diethylamine, dipropylamine, benzylamine, aniline, pyridine, piperidine, pyrrolidine. In the context of the present invention, tetraalkylammonium hydroxides are especially preferred. In particular, tetrapropylammonium hydroxide, more preferably tetra-n-propylammonium hydroxide is employed where a titanium zeolite having MFI structure, also known as titanium silicalite-1 (TS-1) is prepared.

In a preferred embodiment of the process according to the invention, the at least one pore forming agent is removed in a later step by calcination, as described below.

Typically, the synthesis of the titanium zeolite is carried out batchwise in an autoclave so that the reaction suspension is subjected at autogenous pressure for a number of hours or a few days until the titanium zeolite is obtained. According to a preferred embodiment of the present invention, the synthesis generally proceeds at elevated temperatures wherein the temperatures during the hydrothermal crystallization step are typically in the range of from 150 to 200° C., preferably in the range of from 160 to 180° C. Usually, the reaction is carried out for a time in the range of a few hours to several days, preferably for a time in the range of from 12 h to 48 h, more preferably from 20 to 30 h.

It is further conceivable to add seed crystals to the synthesis batches. Such an addition of seed crystals, which is well known in the art, can enhance the crystallization of zeolites and increase the crystallization rate. When used, the seed crystals may be crystals of the desired titanium zeolite, or crystals of a different titanium zeolite.

According to an embodiment of the present invention, the crystalline titanium zeolite obtained, is separated off from the reaction suspension, optionally washed and dried.

All methods known for the separation of the crystalline titanium zeolite from the suspension can be employed. Inter alia, filtration, ultra-filtration, diafiltration and centrifugation methods should be mentioned.

In case the crystalline titanium zeolite obtained is washed, said washing step can be carried out employing any suitable wash substance, such as, for example, water, alcohols, such as for example, methanol, ethanol, or methanol and propanol, or ethanol and propanol, or methanol and ethanol and propanol, or mixtures of water and at least one alcohol, such as, for example, water and ethanol or water and methanol, or water and ethanol, or eater and propanol, or water and methanol and ethanol, or water and methanol and propanol, or water and ethanol and propanol or water and ethanol and methanol and propanol. Water or a mixture of water and at least one alcohol, preferably water and ethanol, are used as wash substance.

In addition to or instead of the at least one wash process, the separated titanium zeolite can also be treated with a concentrated or diluted acid or a mixture of two or more acids.

If the titanium zeolite is subjected to washing and/or treatment with at least one acid, at least one drying step, as described below, follows according to a particularly preferred embodiment of the present invention.

Drying of the crystalline titanium zeolite is effected at temperatures, in general, in the range of from 80 to 160° C., preferably from 90 to 145° C., particularly preferably from 100 to 130° C.

Instead of the above mentioned separation methods, such as, inter alia, filtration, ultra-filtration, diafiltration and centrifugation methods, the suspension may, according to an alternative embodiment, also be subjected to spray methods, as for example spray-granulation and spray-drying.

If the separation of the crystalline titanium zeolite is carried out by means of spray method, the separating and drying step can be combined to a single step. In such case, either the reaction suspension as such or a concentrated reaction suspension can be employed. Additionally, it is possible to add a suitable additive as for example at least one suitable binder and/or at least one pore forming agent to the suspension—either to the reaction suspension as such or to the concentrated suspension—prior to spray drying or spray granulation. Suitable binders are described in detail below. As pore forming agent all pore forming agents described above can be used. In case the suspension is spray-dried, the pore forming agent—if added—may be added in two manners. First, the pore forming agent can be added to the reaction mixture prior to spray drying. However, it is also possible to add a portion of the pore forming agent to the reaction mixture prior to spray drying, with the remainder of the pore forming agent being added to the spray dried material.

In case the suspension is first concentrated to enhance the content of the titanium zeolite in the suspension, concentration can be achieved, for example, by evaporating, as for example evaporating under reduced pressure, or by cross flow filtration. Likewise, the suspension can be concentrated by separating said suspension into two fractions, wherein the solid contained in one of both fractions is separated off by filtration, diafiltration, ultrafiltration or centrifugation methods and is suspended after an optional washing step and/or drying step in the other fraction of the suspension. The thus obtained concentrated suspension can then be subjected to spray methods, as for example spray granulation and spray drying.

According to an alternative embodiment of the invention, concentration is achieved by separating the at least one titanium zeolite from the suspension, and re-suspending the titanium zeolite, optionally together with at least one suitable additive as already described above, wherein the titanium zeolite may be subjected to at least one washing step and/or at least one drying step prior to re-suspension. The re-suspended titanium zeolite can then be employed to spraying methods, preferably to spray drying.

Spray-drying is a direct method of drying slurries, suspensions or solutions by feeding a well-dispersed liquid-solid slurry, suspension or solution, often additionally containing a binder, to an atomizer and subsequently flash-drying in a stream of hot air. The atomizer can be of several different types. Most common is wheel atomization which uses high-speed rotation of a wheel or a disc to break up the slurry into droplets that spin out from the wheel into a chamber and are flash-dried prior to hitting the chamber walls. The atomization may also be accomplished by single fluid nozzles which rely on hydrostatic pressure to force the slurry through a small nozzle. Multi-fluid nozzles are also used, where gas pressure is used to force the slurry through the nozzle. The sprayed material obtained using spray drying and spray granulation methods, like for example fluidized-bed drying, can contain solid and/or hollow spheres and can substantially consist of such spheres, which have, for example, a diameter in the range of from 5 to 500 μm or 5 to 300 μm. Single component or multiple component nozzles can be used. The use of a rotating sprayer is also conceivable. Possible inlet temperatures for the used carrier gas are, for example, in the range of from 200 to 600° C., preferably in the range of from 300 to 500° C. The outlet temperature of the carrier gas is, for example, in the range of from 50 to 200° C. Air, lean air or oxygen-nitrogen mixtures with an oxygen content of up to 10 vol.-%, preferably of up to 5 vol. %, more preferably of less than 5 vol. %, as, for example, of up to 2 vol. %, may be mentioned as carrier gases. The spray methods can be carried out in counter-current or co-current flow.

Preferably, in the context of the present invention, the titanium zeolite is separated from the reaction suspension by conventional filtration or centrifugation, optionally dried and/or calcined, and re-suspended, preferably in a mixture, preferably an aqueous mixture of at least one binder material and/or one pore-forming agent. The resulting suspension is then preferably subjected to spray-drying or spray-granulation. The obtained sprayed material may be subjected to an additional washing step, said washing step being carried out as described above. The optionally washed sprayed material is then dried and calcined wherein drying and calcination is preferably carried out as described above.

According to an alternative embodiment of the present invention, the crystallization of the titanium zeolite is effected not before the above described suspension has been spray dried. Therefore, first a suspension is formed comprising the source of silicon oxide, preferably silicon dioxide, the source of titanium oxide, and the template compound capable of forming the titanium zeolite. Then, the suspension is spray-dried, wherein subsequently, optionally additional pore forming agent is added to the spray dried titanium zeolite.

The spray dried titanium zeolite obtained according to the above mentioned processes can, optionally, be subjected to at least one wash process and/or treatment with at least one acid. If at least one wash process and/or treatment with at least one acid is carried out, preferably at least one drying step and/or at least one calcination step follows.

The at least one crystalline titanium zeolite, optionally obtained by spraying methods, can further be subjected to at least one calcination step, which is carried out according to a preferred embodiment of the invention subsequent to the drying step, or instead of the drying step. The at least one calcination step is carried out at temperatures in general in the range of from 350-750° C., preferably form 400-700° C., particularly preferably from 450-650° C.

The calcination of the crystalline titanium zeolite can be effected under any suitable gas atmosphere, wherein air and/or lean air is preferred. Furthermore, the calcinations is preferably carried out in a muffle furnace, rotary cone and/or a belt calcination furnace, wherein the calcination is generally carried out for one hour or more, for example for a time in the range of from 1 to 24 or from 4 to 12 hours. It is possible in the process according to the present invention, for example, to calcine the zeolite material once, twice or more often for in each case at least one hour, for example in each case from 4 h to 12 h, preferably from 4 h to 8 h, wherein it is possible to keep the temperatures during the calcination step constant or to change the temperatures continuously or discontinuously. If calcination is effected twice or more often, the calcination temperatures in the individual steps may be different or identical.

Thus, a preferred embodiment of the present invention relates to a process as described above, wherein the titanium zeolite separated off from the suspension, for example by filtration or spray drying, is washed with a suitable wash substance, and subsequently subjected to at least one drying step. Drying is effected at temperatures, in general, in the range of from 80 to 160° C., preferably from 90 to 145° C., particularly preferably from 100 to 130° C. Most preferably, after drying, a calcinations step is performed. The step is carried out at temperatures in general in the range of from 350-750° C., preferably form 400-700° C., particularly preferably from 450-650° C.

The crystalline titanium zeolite, prepared as described above, can be directly employed as catalyst in step (ii). Optionally, a mixture of two or more different crystalline titanium zeolites, which differ, for example, in their zeolite structure and/or their titanium content is employed as catalyst. However, it is it often desired to employ not the crystalline material per se as catalyst but the crystalline material processed to give a molding comprising the at least one titanium zeolite. Thus, according to a preferred embodiment, a molding comprising at least one titanium zeolite, as described above, is employed as catalyst.

In general, in case a molding is employed as catalyst, said catalyst may comprise all conceivable further compounds in addition to the titanium zeolite according to the invention, for example, inter alia, at least one binder and/or at least one pore forming agent. Furthermore the catalyst may comprise at least one pasting agent instead of the at least one binder and/or the at least one pore forming agent or in addition to the at least one binder and/or the at least one pore forming agent.

As binder all compounds are suitable, which provide adhesion and/or cohesion between the at least one titanium zeolite to be shaped which goes beyond the physisorption which may be present without a binder. Examples of such binders are metal oxides, such as, for example, $SiO_2$, $Al_2O_3$, $TiO_2$, $ZrO_2$ or MgO or clays or mixtures of two or more of these compounds. Clay minerals and naturally occurring or synthetically produced aluminas, such as, for example, alpha-, beta-, gamma-, delta-, eta-, kappa-, chi- or theta-alumina and their inorganic or organometallic precursor compounds, such as, for example, gibbsite, bayerite, boehmite or pseudoboehmite or trialkoxyaluminates, such as, for example, aluminum tri-isopropylate, are particularly preferred as $Al_2O_3$ binders. Further preferred binders are amphiphilic compounds having a polar and a nonpolar moiety and graphite. Further binders are, for example, clays, such as, for example, montmorillonites, kaolins, metakaoline, hectorite, bentonites, halloysites, dickites, nacrites or anaxites.

These binders can be used as such. It is also within the scope of the present invention to use compounds from which the binder is formed in at least one further step in the production of the moldings. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate.

In the context of the present invention binders which either completely or partly comprise $SiO_2$, or which are a precursor of $SiO_2$, from which $SiO_2$ is formed in at least one further step, are very particularly preferred. In this context, both colloidal silica and so-called "wet process" silica and so-called "dry process" silica can be used. Particularly preferably this silica is amorphous silica, the size of the silica particles being, for example, in the range of from 5 to 100 nm and the surface area of the silica particles being in the range of from 50 to 500 m$^2$/g.

Colloidal silica, preferably as an alkaline and/or ammoniacal solution, more preferably as an ammoniacal solution, is commercially available, inter alia, for example as Ludox®, Syton®, Nalco® or Snowtex®. "Wet process" silica is commercially available, inter alia, for example as Hi-Sil®, Ultrasil®, Vulcasil®, Santocel®, Valron-Estersil®, Tokusil® or Nipsil®. "Dry process" silica is commercially available, inter alia, for example as Aerosil®, Reolosil®, Cab-O-Sil®, Fransil® or ArcSilica®. Inter alia, an ammoniacal solution of colloidal silica is preferred in the present invention. Accordingly, the present invention also describes a catalyst containing a molding, as described above, said molding comprising a titanium zeolite as described above and additionally SiO$_2$ as binder material wherein the binder used according to (I) is a binder comprising or forming SiO$_2$.

However, in the context of the present invention, the titanium zeolite can also be shaped without using a binder.

Thus the present invention also relates to a process, wherein in (i) the at least one titanium zeolite is shaped to give a molding comprising the at least one titanium zeolite and preferably at least one binder, in particular a silica binder.

If desired at least on pore forming agent can be added to the mixture of titanium zeolite and at least one binder or at least binder-precursor, for further processing and for the formation of the catalyst shaped body. Pore forming agents which may be used in the shaping process according to the invention are all compounds which, with regard to the molding produced, provide a specific pore size and/or a specific pore size distribution and/or certain pore volumes. In particular pore forming agents which provide, with regard to the molding produced, micropores and/or micropores, in particular mesopores and micropores.

Thus, the invention also relates to a process, as described above, wherein in (i), the titanium zeolite is shaped to obtain a molding comprising the titanium zeolite and preferably at least one binder, in particular a silica binder, the molding in particular having micropores and mesopores.

As regards examples for pore forming agents which may be used, reference is made to the pore forming agents already mentioned above. Preferably, the pore forming agents used in the shaping process of the invention are polymers which are dispersible, suspendable or emulsifiable in water or in aqueous solvent mixtures. Especially preferred polymers are polymeric vinyl compounds, such as, for example, polyalkylene oxides, such as polyethylene oxides, polystyrene, polyacrylates, polymethacrylates, polyolefins, polyamides and polyesters, carbohydrates, such as, for example, cellulose or cellulose derivatives, such as, for example, methyl cellulose, or sugars or natural fibers. Further suitable pore forming agents are, for example, pulp or graphite.

If desired for the pore size distribution to be achieved, a mixture of two or more pore forming agents may be used. In a particularly preferred embodiment of the process according to the invention, as described below, the pore forming agents are removed by calcination to give the porous catalyst shaped body. Preferably, pore forming agents which provide mesopores and/or micropores, particularly preferably mesopores, are added to the mixture of at least one binder and titanium zeolite for shaping the titanium zeolite.

However, in the context of the present invention, the titanium zeolite can also be shaped to obtain a catalyst shaped body without using a pore forming agent.

Besides binder and optionally pore forming agent it is as well possible to add additional components, for example at least one pasting agent, to the mixture which is shaped to obtain a catalyst shaped body prior to step (i).

If at least one pasting agent is used in the process of the invention, said pasting agent is used either instead of or in addition to the at least one pore forming agent. In particular, compounds which also act as pore forming agents can be used as pasting agent. Pasting agents which may be used are all compounds known to be suitable for this purpose. These are preferably organic, in particular hydrophilic polymers, such as, for example, cellulose, cellulose derivatives, such as, for example, methyl cellulose, and starch, such as, for example, potato starch, wallpaper plaster, polyacrylates, polymethacrylates, polyvinyl alcohol, polyvinylpyrrolidone, polyisobutene or polytetrahydrofuran. The use of water, alcohols or glycols or mixtures thereof, such as mixtures of water and alcohol, or water and glycol, such as for example water and methanol, or water and ethanol, or water and propanol, or water and propylenglycol, as pasting agents may be mentioned. Preferably, cellulose, cellulose derivatives, water and mixtures of two or more of these compounds, such as water and cellulose or water and cellulose derivatives are used as pasting agent. In a particularly preferred embodiment of the process according to the invention, the at least one pasting agents is removed by calcination, as further described below, to give the molding.

According to a further embodiment of the present invention, at least one acidic additive can be added to the mixture which is shaped to obtain the molding. If an acidic additive is used, organic acidic compounds which can be removed by calcination, are preferred. In this context carboxylic acids, such as, for example, formic acid, oxalic acid and/or citric acid, may be mentioned. It is also possible to use two or more of these acidic compounds.

The order of addition of the components to the mixture which is shaped to obtain the molding is not critical. If for example, a combination of a binder, a pore forming agent, a pasting agent and optionally at least one acidic compound is employed, it is possible both first to add the at least one binder then the at least one pore forming agent, the at least one acidic compound and finally the at least one pasting agent and to interchange the sequence with regard to the at least one binder, the at least one pore forming agent, the at least one acidic compound and the at least one pasting agent.

After the addition of at least one binder and/or at least one pasting agent and/or at least one pore forming agent and/or at least one acidic additive to the mixture comprising the titanium zeolite, the mixture is typically homogenized for 10 to 180 minutes. Inter alia, kneaders, edge mills or extruders are particularly preferably used for the homogenization. The mixture is preferably kneaded. On an industrial scale, grinding in an edge mill is preferred for the homogenization.

The homogenization is, as a rule, carried out at temperatures in the range of from about 10° C. to the boiling point of the pasting agent and atmospheric pressure or slightly superatmospheric pressure. Optionally, at least one of the compounds described above can then be added. The mixture thus obtained is homogenized, preferably kneaded, until an extrudable plastic material is formed.

The homogenized mixture is then shaped to obtain a molding. All known suitable shaping methods, such as extrusion, spray drying, spray granulation, briquetting, i.e. mechanical compression with or without addition of additional binder or pelleting, i.e. compacting by circular and/or rotary movements, may be employed.

Preferred shaping methods are those in which conventional extruders are employed to shape the mixture comprising the at least on titanium zeolite. Thus, for example extrudates having a diameter of from 1 to 10 mm and preferably of from 2 to 5 mm are obtained. Such extrusion apparatuses are described, for example, in "Ullmann's Enzyklopädie der Technischen Chemie", 4$^{th}$ edition, vol. 2, page 295 et seq., 1972. In addition to the use of an extruder, an extrusion press can also be used for the preparation of the moldings. The shape of the moldings produced according to the invention can be chosen as desired. In particular, inter alia, spheres, oval shapes, cylinders or tablets are possible. Likewise, hollow structures, as for example hollow cylinders or honeycomb formed structures or also star-shaped geometries may be mentioned.

The shaping can take place at ambient pressure or at a pressure higher than ambient pressure, for example in a pressure range of from 1 bar to several hundred bar. Furthermore, the compacting can take place at ambient temperature or at a temperature higher than ambient temperature, for example in a temperature range of from 20 to 300° C. If drying and/or calcining are part of the shaping step, temperatures of up to 600° C. are conceivable. Finally, the compacting can take place in an ambient atmosphere or in a controlled atmosphere. Controlled atmospheres are, for example, inert gas atmospheres, reducing atmospheres and/or oxidizing atmospheres.

When shaping is carried out, the shaping step is preferably followed by at least one drying step. This at least one drying step is carried out at temperatures in the range of in general from 80 to 160° C., preferably of from 90 to 145° C. and particularly preferably of from 100 to 130° C., usually for 6 h or more, for example in the range of from 6 to 24 h. However, depending on the moisture content of the material to be dried, shorter drying times, such as, for example, about 1, 2, 3, 4 or 5 h are also possible.

Before and/or after the drying step, the preferably obtained extrudate can, for example, be comminuted. Preferably granules or chips having a particle diameter of from 0.1 to 5 mm, in particular of from 0.5 to 2 mm, are obtained thereby.

According to a preferred embodiment of the present invention, the drying of the moldings, respectively, is preferably followed by at least one calcination step. Calcination is carried out at temperatures in general in the range of from 350-750° C., preferably form 400-700° C., particularly preferably from 450-650° C. The calcination can be effected under any suitable gas atmosphere, wherein air and/or lean air are preferred. Furthermore, the calcination is preferably carried out in a muffle furnace, a rotary kiln and/or a belt calcining furnace, wherein the duration of calcination is in general 1 h or more, for example in the range of from 1 to 24 h or in the range of from 3 to 12 h. In the process according to the invention, it is accordingly possible, for example, to calcine the catalyst shaped body once, twice or more often for in each case at least 1 h, such as, for example, in each case in the range of from 3 to 12 h, wherein it is possible for the temperatures during a calcination step to remain constant or to be changed continuously or discontinuously. If calcination is effected twice or more often, the calcination temperatures in the individual steps may be different or identical.

Accordingly, the present invention also describes a process for the preparation of a catalyst for the use in a hydrocarbon conversion reaction said catalyst containing a molding comprising at least one titanium zeolite and carbonaceous material in a range of from 0.01 to 0.05% by weight based on the total weight of the titanium zeolite contained in the catalyst, the process comprising (i) preparing a catalyst containing a molding, said molding comprising the at least one titanium zeolite and a silica binder, the catalyst being subsequently dried and calcined (ii) depositing carbonaceous material on the catalyst according to (i) in the range of from 0.01-0.5% by weight based on the total weight of the titanium zeolite contained in the catalyst, by contacting the catalyst with a hydrocarbon in an inert atmosphere to obtain the carbonaceous material containing catalyst;

wherein in (i), the catalyst is not contacted with an oxygen containing gas.

According to a particularly preferred embodiment of the process according to the invention, the catalyst, is subjected to a hydrothermal treatment prior to treatment with the hydrocarbon according to (ii). Hydrothermal treatment can be carried out employing any suitable method known to those skilled in the art. Thus, the catalyst or catalyst shaped in general is contacted with water or water vapor.

Typically, said hydrothermal treatment is carried out by charging the catalyst or according to the invention together with water into an autoclave, heating the slurry to a temperature in the range of from 100 to 200° C., preferably in the range of from 120 to 150° C. at a pressure in the range of from 1.5 to 5 bar, preferably in the range of from 2 to 3 bar, for a period in the range of from 1 to 48 hours, preferably in the range of from 24 to 48 hours. Typically at least one washing step, preferably with water as wash substance, follows.

After the treatment with water the catalyst is being preferably dried and/or calcined, wherein drying and calcination is carried out as already described above.

Accordingly, the present invention also relates a process as described above, wherein, prior to (ii), the catalyst is subjected to hydrothermal treatment, the hydrothermal treatment preferably comprising (I) treating the catalyst with water in an autoclave, preferably at a pressure of from 1.5 to 5 bar, at a temperature in the range of 100 to 200° C. and for a period of from 1 to 48 hours;
(II) drying the catalyst, and
(III) calcining the catalyst.

According to a preferred embodiment of the invention, the hydrothermal treatment is carried out by stirring the catalyst shaped body in an autoclave, wherein the stirring rate is adjusted to a stirring rate such that to avoid attrition as far as possible. If the catalyst is used in form of cylindrical extrudates, however, some attrition is desired to achieve cylindrical extrudates having rounded edges. With such extrudates having rounded edges, a higher bulk density can be achieved, for example for a possible use of the extrudates as fixed-bed catalyst in a suitable reactor such as in a tube reactor. Furthermore, the dust formation of said catalysts in the further process, thus in step (ii) and in the hydrocarbon conversion reaction, is reduced.

The attrited parts of the catalyst can be combined according to a further embodiment of the invention and be reused as additive to the mixture to be shaped to obtain a molding, as described above, or as seed crystals in the process for the preparation of the at least one titanium zeolite.

Thus, according to an embodiment of the present invention, the at least one titanium zeolite according to (i) is combined with at least one binder, optionally also with one or more additional additives as described above, and the attrited parts of the catalyst derived from the hydrothermal treatment of said catalyst and is shaped to obtain a molding. The titanium zeolite contained in the attrited parts may have the same or a different structure as the titanium zeolite with which it is combined to produce the moldings. Shaping can be carried out as described above, thus for example extrusion or spray methods can be applied. The molding, i.e. the catalyst, thus obtained can be again subjected to hydrothermal treatment prior to step (ii).

Accordingly the invention also relates to a catalyst, and a catalyst obtainable by the process, as described above, having micropores and mesopores, comprising from 49.5 to 80%, preferably 69.5 to 80% by weight of a titanium zeolite, based on the total weight of the catalyst, from 19.5 to 50%, preferably from 19.5 to 30% by weight of at least one binder, preferably a silica binder, based on the total weight of the catalyst shaped body, and from 0.01 to 0.5% by weight of carbonaceous material, based on the weight of titanium zeolite, wherein the at least one titanium zeolite, is titanium zeolite having the structure MFI, MEL, MWW, BEA or FER or a mixed structure of two or more thereof.

Subsequent to step (i), carbonaceous material is deposited on the catalyst according to (ii) by contacting the catalyst with a hydrocarbon in an inert atmosphere.

The term "hydrocarbon" refers to any compound which comprises hydrogen and carbon. Typically the hydrocarbon employed in step (ii) corresponds to the hydrocarbon being converted in the hydrocarbon conversion reaction, in which the catalyst obtained in (ii) is used. Thus, the invention also relates to a process, wherein in (ii), the catalyst is employed for the conversion of a hydrocarbon, which hydrocarbon corresponds to the hydrocarbon employed in (ii). However, both hydrocarbons may as well be different. Examples of hydrocarbons that may be used in step (ii) of the process of the invention include non-polar aromatic compounds such as benzene, toluene, ethyl benzene, xylene, and saturated aliphatic hydrocarbons such as alkenes and alkynes, preferably $C_2$-$C_{15}$-alkenes or alkynes or alkanes, and polar aliphatic hydrocarbons such as alcohols. Preferably, olefins are used as hydrocarbons. Examples of olefins employed include, without limitation, propylene, 1-butene, 2-butene, 2-methylpropylene, 1-pentene, 2-pentene, 2-methyl 1-butene, 2-methyl 2-butene, 1-hexene, 2-hexene, 3-hexene, the various isomers of methylpentene, ethylbutane, heptene, methylhexene, methylpentene, propylbutane, the octenes, including preferably 1-octene, and other higher analogues of theses; as well as butadiene, cyclopentadiene, dicyclopentadiene, styrene, methyl styrene, divinylbenzene, allyl chloride, allyl alcohol, allyl ether, allylethyl ether, allyl butyrate, allyl acetate, allyl benzene, allylphenyl ether, allylpropyl ether, and allylanisole.

Preferably, the hydrocarbon is a $C_3$-$C_{12}$ olefin, more preferably a $C_3$-$C_8$ olefin. Most preferably, the olefin is propylene $C_3H_6$. The term hydrocarbon as used may also comprise a mixture of two or more of the above mentioned compounds. It has to be understood that the term hydrocarbons also includes mixtures of any of the above mentioned compounds or of two or more of the above mentioned compounds having minor amounts of impurities. If for example propylene is used, the propylene may be from any source and may be any grade suitable for the process of the invention. Suitable grades include, but are not limited to, polymer grade propylene (generally greater than or equal to 99% propylene), chemical grade propylene (general greater then or equal to 94% propylene), and refinery grade propylene (generally greater than or equal to 60% propylene). Most preferably, chemical grade propylene is used for the process of the present invention, with the remaining 6% or less impurities being mostly propane. Thus, according to the invention, the term propylene also comprises mixture of propylene with small amounts of propane and optionally further minor amounts of impurities, such as mixtures of at least 94% of propylene and 6% or less of propane.

Accordingly, the invention also relates to a process, and a catalyst obtainable or obtained by said process, wherein the hydrocarbon employed in (ii) is an olefin, preferably propylene.

As "inert atmosphere" conventional inert gases, such as, for example nitrogen, carbon monoxide, carbon dioxide, helium and argon or mixtures of two or more thereof, may be used. Preferably, nitrogen is used as inert atmosphere. It has to be understood, that the inert gases may also comprise usual amounts of impurities, however they contain substantially no oxidizing agent, in particular no hydroperoxide or oxygen.

It is important to carefully control the conditions employed in step (ii), such as the temperature and flow rate of the fluid employed so as to obtain the desired catalyst having the specific amount of carbonaceous material deposited thereon.

According to the invention, step (ii) is carried out at elevated temperature, preferably at a temperature in the range of from 100 to 500° C., more preferably at a temperature in the range of from 200 to 490° C., even more preferably at a temperature in the range of from 300 to 480° C., more preferably at a temperature in the range of from 400 to 470° C., and most preferably at a temperature in the range of from 420 to 460° C. It is in principle possible to initially heat up the catalyst in an inert atmosphere and subsequently contact the catalyst at this temperature with the hydrocarbon containing fluid. However, it is likewise conceivable to heat up the catalyst directly in the presence of the hydrocarbon containing fluid without such a preheating in an inert atmosphere. To reach the above mentioned elevated temperature, the temperature can be increased continuously or stepwise prior to or during contacting the catalyst with the fluid. According to a preferred embodiment, the catalyst is heated to the desired temperature in an inert atmosphere, preferably in a nitrogen atmosphere, and once the temperature is reached, is contacted with the hydrocarbon. While being contacted with the hydrocarbon, contacting the catalyst with nitrogen is preferably continued. The catalyst is heated under flow of air or an inert gas, preferably an inert gas, more preferably nitrogen, and then the fluid containing the hydrocarbon and the inert atmosphere stream are passed over the catalyst for a time sufficient to deposit carbonaceous material in the range of from 0.01 to 0.5% by weight, preferably of from 0.01 to 0.3% by weight, most preferably of from 0.01 to 0.1% by weight based on the total weight of the titanium zeolite contained in the catalyst, on said catalyst. The catalyst is typically contacted with the fluid containing the hydrocarbon and the inert atmosphere for a time in the range of from 1 to 72 h, preferably from 6 to 48 h, and most preferably in the range of from 12 to 36 h Typically, the fluid is contacted with the catalyst at a pressure in the range of from 0.5 to 2 bar, preferably in the range of from 0.75 to 1.5 bar, most preferably in the range of from 0.95 to 1.05 bar. i.e. essentially at ambient pressure.

The flow rate at which the inert atmosphere, preferably nitrogen, is charged to the zone, in which step (ii) is carried out, preferably to the reactor, is typically in the range of from 200 to 1000 Nl/h (norm liter per hour), preferably of from 400 to 900 Nl/h, more preferably from 600 to 800 Nl/h.

The flow rate at which the fluid comprising the hydrocarbon in an inert atmosphere is charged to the zone, in which step (ii) is carried out, preferably to the reactor, is typically in the range of from 10 to 100 Nl/h (norm liter per hour), preferably of from 15 to 90 Nl/h, more preferably from 20 to 80 Nl/h.

The fluid containing the hydrocarbon in an inert atmosphere, preferably the hydrocarbon in nitrogen, can be applied as gaseous, liquid or supercritical fluid, wherein according to a preferred embodiment the fluid applied in (ii) is gaseous.

Step (ii) is preferably carried in a reactor wherein any suitable reactor may be used. Suitable reactors include batch, fixed-bed, transport-bed, fluidized-bed, moving-bed, shell and tube, and trickled-bed reactors, as well as continuous and intermittent-flow and swing reactor designs, preferably fixed-bed. Preferably, step (ii) is carried out in the same reactor, which is employed for the following hydrocarbon conversion process.

Preferably, the catalyst obtained in step (ii) is directly employed in the hydrocarbon conversion reaction. The term "directly" as used in this context refers to an embodiment wherein that no carbonaceous material is burned off from the catalyst, by for example contacting the catalyst with an oxygen containing atmosphere, between depositing carbonaceous material on the catalyst according to (ii) and the use of said catalyst in the hydrocarbon conversion reaction. Likewise, after step (ii), the catalyst is not subjected to an additional heat treating step, wherein the hydrocarbon is treated with the inert gas at high temperatures, such as temperatures above 300° C. However, the term "directly" includes embodiments wherein the catalyst is, for example, purged before using the catalyst in the hydrocarbon conversion process. Such an additional purging step is preferably carried out if the hydrocarbon contained in the fluid according to (ii) does not correspond to the hydrocarbon to be converted in the hydrocarbon conversion reaction, so that a contact between these different hydrocarbons is minimized, preferably eliminated. If the hydrocarbon contained in the fluid according to (ii) corresponds to the hydrocarbon to be converted in the hydrocarbon conversion reaction, preferably no purging step is carried out. The purge media employed should not have any adverse effect on the catalyst or the subsequent hydrocarbon conversion to be carried out. Preferably, the purge media is, if employed, gaseous, and is employed in an amount effective to remove substantially all of the at least one hydrocarbon contained in the fluid according to (ii). As purge gas, typically an inert gas or a mixture of inert gases is employed.

According to a preferred embodiment of the present invention, the catalyst is employed in (iii) for the conversion of a hydrocarbon, which hydrocarbon corresponds to the hydrocarbon employed in (ii). In case the hydrocarbon employed in (ii) corresponds to the hydrocarbon being converted in the hydrocarbon conversion reaction, the conversion reaction can in principle be started directly after step (ii), merely by changing the conditions at the end of the contacting treatment. In this case, typically no purging step is carried out. This embodiment has the advantage, that purging time and costs can be saved.

Thus, the invention also relates to a process, wherein in (ii), the catalyst is employed for the conversion of a hydrocarbon, which hydrocarbon corresponds to the hydrocarbon employed in (ii).

As already described above, the conditions employed in step (ii) have to be carefully adjusted to control the amount of carbonaceous material deposited on the catalyst such as to obtain a catalyst having the above mentioned improved catalytic properties. It should be pointed out, that instead of a depositing step, wherein at least a portion if not all of the catalytic activity is lost, which has to be followed by a treatment with an oxygen containing gas, or instead of a depositing step followed by a treatment, wherein the carbonaceous material has to be heated up for a while to activate the catalyst, the depositing step according to (ii) of the invention directly yields, without further treatment, in the catalyst having the desired amount of carbonaceous deposits and the improved catalytic activity.

Said catalyst is characterized by an amount of carbonaceous material being in the range of from 0.01 to 0.5% by weight, preferably of from 0.01 to 0.1% by weight, most preferably of from 0.03 to 0.04% by weight based on the total weight of the titanium zeolite contained in the catalyst.

Surprisingly, in particular as far as the use of an inventive TS-1 catalyst for the epoxidation of propylene, preferably using hydrogen peroxide as oxidation agent in the presence of preferably methanol as solvent is concerned, it was found that said catalyst having a certain amount of carbonaceous material deposited thereon is especially suitable. Even more surprisingly, it was found that for this particular embodiment, the amount of carbonaceous material should not be too high. Consequently, it was found that catalysts, in particular TS-1 catalysts used as catalysts for the epoxidation of propylene preferably using hydrogen peroxide as oxidation agent in the presence of preferably methanol as solvent, the amount of carbonaceous material should be in the range of from 0.01 to 0.06% by weight, preferably in the range of from 0.02 to 0.05% by weight, and more preferably in the range of from 0.03 to 0.04% by weight.

The amount of carbonaceous material in the catalyst is determined by total organic carbon (TOC) analysis.

Typically, the catalyst as well as the catalyst obtainable by the process according to the invention, have a crush strength being higher compared to catalysts of the same composition which have not been contacted with a hydrocarbon. In the present invention, the crush strength described above was determined using an apparatus from Zwick, type BZ2.5/TS1S with a preliminary force of 0.5 N, a shear rate under preliminary force of 10 mm/min and a subsequent testing rate of 1.6 mm/min. The apparatus had a fixed turntable and freely movable ram with built-in blade of 0.3 mm thickness. The movable ram with the blade was connected to a load cell for force pick-up and, during the measurement, moved toward the fixed turntable on which the catalyst to be investigated lay. The tester was controlled by means of a computer which registered and evaluated the results of the measurements. The values obtained are the mean value of the measurements for 10 catalysts in each case. The catalyst had a cylindrical geometry, their mean length corresponding approximately to twice to three times the diameter, and was loaded with the 0.3 mm thick blade with increasing force until the catalyst had been cut through. The blade was applied to the catalyst perpendicularly to the longitudinal axis of the catalyst shaped body. The force required for this purpose is the cutting hardness (unit N).

Preferably, the moldings obtained according to the process of the present invention containing the carbonaceous material have a cutting hardness of at least 22 N, preferably from 22 to 30 N, and more preferably from 22 to 25 N.

The catalyst according to (i) and the catalyst according to (ii), not only differ in their content of carbonaceous material and crush strength but also, for example, in their colour, which changes during the depositing process. Generally, the catalyst having a higher amount of carbonaceous material deposited thereon tends to have a darker shade of grey than catalysts having a lower amount of carbonaceous material deposited thereon.

Conversions which can be catalyzed by the catalyst according to the invention are, for example, hydrogenations, dehydrogenations, dehydrogenations, oxidations, epoxidations, polymerization reactions, aminations, hydrations and dehydrations, nucleophilic and electrophilic substitution reactions, addition and elimination reactions, double-bond and skeletal isomerizations, dihydrocyclizations, hydroxylations of heteroaromatics, epoxide-aldehyde rearrangements, metatheses, olefin preparations for methanol, dielsalder reactions, formation of carbon-carbon double-bonds such as, for example, olefin dimerizations or olefin trimerizations, and condensation reactions of the aldocondensation type. Depending on the hydrocarbon to be reacted, the catalytic reactions can be carried out in the gas or liquid phase or in the supercritical phase. Suitable hydrocarbons are non-polar aromatic compounds such as benzene, toluene, ethyl benzene, xylene, and saturated aliphatic hydrocarbons such as alkenes and alkynes, preferably $C_2$-$C_{15}$-alkenes or alkynes or alkanes, and polar alphatic hydrocarbons such as alcohols.

The catalyst according to the invention is particularly suitable for the oxidation of a hydrocarbon, preferably for the oxidation of an olefin. Examples of suitable olefins include, without limitation, propylene, 1-butene, 2-butene, 2-methylpropylene, 1-pentene, 2-pentene, 2-methyl 1-butene, 2-methyl-2-butene, 1-hexene, 2-hexene, 3-hexene, the various isomers of methylpentene, ethylbutane, heptene, methylhexene, methylpentene, propylbutane, the octenes, including preferably 1-octene, and other higher analogues of theses; as well as butadiene, cyclopentadiene, dicyclopentadiene, styrene, methyl styrene, divinylbenzene, allyl chloride, allyl alcohol, allyl ether, allylethyl ether, allyl butyrate, allyl acetate, allylbenzene, allylphenyl ether, allylpropyl ether, and allylanisole. Preferably, the olefin is a $C_3$-$C_{12}$-olefin, more preferably a $C_3$-$C_8$-olefin. Most preferably, the olefin is propylene. Particularly preferably, the catalyst is used for the oxidation of propylene, more preferably for the epoxidation of propylene.

Accordingly, the invention also relates to the use of a catalyst, as described above, for the conversion, preferably the oxidation, of a hydrocarbon, preferably an olefin, more preferably propylene, in particular the epoxidation of propylene.

Moreover, the invention relates to said use, wherein the process for the conversion of a hydrocarbon is a process for the preparation of propylene oxide in the presence of a catalyst containing at least one titanium zeolite and carbonaceous material, the catalyst comprising said carbonaceous material in a range of from 0.01 to 0.5% by weight based on the total weight of titanium zeolite, the process comprising
(i) providing a catalyst containing the titanium zeolite;
(ii) depositing carbonaceous material on the catalyst according to (i) in the range of from 0.01 to 0.5% by weight based on the total weight of titanium zeolite contained in the catalyst by contacting said catalyst, prior to using the catalyst in said hydrocarbon conversion reaction, with a fluid containing at least one hydrocarbon in an inert atmosphere, to obtain the carbonaceous material containing catalyst,
(iii) contacting the catalyst obtained according to (ii) with a reaction mixture comprising propylene, hydroperoxide, and at least one solvent,
wherein in (ii), the catalyst is not contacted with an oxygen containing gas.

Further, the invention relates to said use, wherein in (iii), the catalyst is a titanium silicalite-1 catalyst, the hydroperoxide is hydrogen peroxide and the solvent is methanol.

Also, the invention relates to said use, wherein the catalyst contains the carbonaceous material in an amount of from 0.01 to 0.1% by weight, preferably from 0.01 to 0.06% by weight, more preferably from 0.02 to 0.05% by weight, more preferably from 0.03 to 0.04%, based on the total weight of titanium zeolite contained in the catalyst, and wherein in (ii), the carbonaceous material is deposited on the catalyst according to (i) in an amount of from 0.01 to 0.1% by weight, preferably from 0.01 to 0.06% by weight, more preferably from 0.02 to 0.05% by weight, more preferably from 0.03 to 0.04% by weight, based on the total weight of titanium zeolite contained in the catalyst.

In case the chemical reaction according to (iii) is the epoxidation of propylene, preferably propylene is used in step (ii) as well.

Again, the term propylene also encompasses propylene from any source and with any grade, for example chemical grade or polymer grade propylene. According to the invention, propylene having the same grade or different grade may be used in step (ii) and in the conversion reaction, respectively.

According to a preferred embodiment, the propylene stream used in step (ii) may also be recycled, optionally after purification steps, into the hydrocarbon conversion reaction, thus preferably into the epoxidation reaction.

If the chemical reaction according to (iii) is an epoxidation of an olefin, preferably of propylene, in principle any suitable oxidizing agent can be used in the context of the present invention. The oxidizing agent can be, for example, oxygen or any suitable peroxide. Preferably, hydroperoxides, as for example tertiary hydroperoxides, are used in the context of the present invention. Particularly preferably hydrogen peroxide is used. Preferably at least one alcohol, such as such, for example, as methanol, or nitrils, such as, for example, acetonitrile or mixtures thereof, optionally additionally comprising water, maybe used.

Preferably methanol is used as solvent in combination with hydrogen peroxide as oxidant, especially in case propylene is converted to propylene oxide in the presence of a catalyst containing a titanium zeolite having MFI structure.

Accordingly, the present invention also relates to a process for the epoxidation of propylene, comprising
(i) preparing a catalyst containing a titanium zeolite, preferably a titanium zeolite having MFI structure;
(ii) depositing carbonaceous material on the catalyst obtained according to (i) by contacting the catalyst with propylene in an inert atmosphere;
(iii) directly employing the catalyst obtained according to (ii) in the epoxidation of propylene, preferably using methanol as solvent and hydroperoxide as oxidant;
wherein the catalyst obtained according to (iii) contains carbonaceous material in the range of from 0.01 to 0.5% by weight, preferably of from 0.01 to 0.1% by weight, most preferably of from 0.03 to 0.04% by weight based on the total weight of the titanium zeolite contained in the catalyst, the content of carbonaceous material being determined by total organic carbon analysis.

Further, the invention relates to said process for the conversion of a hydrocarbon, wherein the process for the conversion of a hydrocarbon is a process for the preparation of propylene oxide in the presence of a catalyst containing at least one titanium zeolite and carbonaceous material, the catalyst comprising said carbonaceous material in a range of from 0.01 to 0.5% by weight based on the total weight of titanium zeolite, the process comprising
(i) providing a catalyst containing the titanium zeolite;
(ii) depositing carbonaceous material on the catalyst according to (i) in the range of from 0.01 to 0.5% by weight based on the total weight of titanium zeolite contained in the catalyst by contacting said catalyst, prior to using the catalyst in said hydrocarbon conversion reaction, with a fluid containing at least one hydrocarbon in an inert atmosphere, to obtain the carbonaceous material containing catalyst, (iii) contacting the catalyst obtained according to (ii) with a reaction mixture comprising propylene, hydroperoxide, and at least one solvent, wherein in (ii), the catalyst is not contacted with an oxygen containing gas.

Further, the invention relates to said process for the epoxidation of propylene, wherein in (iii), the catalyst is a titanium silicalite-1 catalyst, the hydroperoxide is hydrogen peroxide and the solvent is methanol.

Also, the invention relates to said process for the epoxidation of propylene, wherein the catalyst contains the carbonaceous material in an amount of from 0.01 to 0.1% by weight, preferably from 0.01 to 0.06% by weight, more preferably from 0.02 to 0.05% by weight, more preferably from 0.03 to 0.04%, based on the total weight of titanium zeolite contained in the catalyst, and wherein in (ii), the carbonaceous material is deposited on the catalyst according to (i) in an amount of from 0.01 to 0.1% by weight, preferably from 0.01 to 0.06% by weight, more preferably from 0.02 to 0.05% by weight, more preferably from 0.03 to 0.04% by weight, based on the total weight of titanium zeolite contained in the catalyst.

Moreover, the invention also relates to propylene oxide obtainable or obtained by said process.

According to the present invention, the process of employing the catalyst obtained according to (ii) in the epoxidation of propylene using methanol as solvent preferably comprises reacting the propylene with hydrogen peroxide in the presence of methanol as solvent in at least two reaction stages to obtain a mixture M comprising propylene oxide, unreacted propylene, methanol and water, wherein between at least two reaction stages, propylene oxide is separated by distillation. Therefore, the inventive process comprises at least the following sequence of stages (a) to (c):

(a) reaction of propylene with hydrogen peroxide to give a mixture comprising propylene oxide and unreacted propylene,
(b) separation of the unreacted propylene from the mixture resulting from stage (i),
(c) reaction of the propylene which has been separated off in stage (ii) with hydrogen peroxide.

Therefore, the epoxidation process can comprise, in addition to stages (a and (c), at least one further reaction stage and, in addition to stage (b), at least one further separation stage. According to a preferred embodiment, the epoxidation process consists of these three stages.

As to stages (a) and (c), there are no specific restrictions as to how the reaction is carried out.

Accordingly, it is possible to carry out one of the reactions stages in batch mode or in semi-continuous mode or in continuous mode and independently thereof, the other reaction stage in batch mode or in semi-continuous mode or in continuous mode. According to an even more preferred embodiment, both reaction stages (a) and (c) are carried out in continuous mode.

Preferably, the epoxidation reaction in stage (i) is carried out in the presence of the catalyst of the present invention. Even more preferably, both stages (a) and (c) are carried out in the presence of the catalyst of the present invention. The reactions in stages (a) and (c) are preferably carried out in suspension or fixed-bed mode, most preferably in fixed-bed mode.

In the inventive process, it is possible to use the same or different types of reactors in stages (a) and (c). Thus, it is possible to carry out one of the reactions stages in an isothermal or adiabatic reactor and the other reaction stage, independently thereof, in an isothermal or adiabatic reactor. The term "reactor" as used in this respect comprises a single reactor, a cascade of at least two serially connected reactors, at least two reactors which are operated in parallel, or a multitude of reactors wherein at least two reactors are serially coupled and wherein at least two reactors are operated in parallel. According to a preferred embodiment, stage (a) of the present invention is carried out in at least two reactors which are operated in parallel, and stage (c) of the present invention is carried out in a single reactor.

Each of the reactors described above, especially the reactors according to the preferred embodiment, can be operated in downflow or in upflow operation mode.

In case the reactors are operated in downflow mode, it is preferred to use fixed-bed reactors which are preferably tubular, multi-tubular or multi-plate reactors, most preferably equipped with at least one cooling jacket. In this case, the epoxidation reaction is carried out at a temperature of from 30 to 80° C., and the temperature profile in the reactors is maintained at a level so that the temperature of the cooling medium in the cooling jackets is at least 40° C. and the maximum temperature in the catalyst bed is 60° C. In case of downflow operation of the reactors, it is possible to chose the reaction conditions such as temperature, pressure, feed rate and relative amounts of starting materials such that the reaction is carried out in a single phase, more preferably in a single liquid phase, or in a multiphase system comprising, for example, 2 or 3 phases. As to the downflow operation mode, it is especially preferred to conduct the epoxidation reaction in a multiphase reaction mixture comprising a liquid aqueous hydrogen peroxide rich phase containing methanol and a liquid organic olefin rich phase, preferably a propene rich phase.

In case the reactors are operated in upflow mode, it is preferred to use fixed-bed reactors. It is still further preferred to use at least two fixed-bed reactors in stage (a) and at least one reactor in stage (c). According to a still further embodiment, the at least two reactors used in stage (a) are serially connected or operated in parallel, more preferably operated in parallel. Generally, it is necessary to equip at least one of the reactors used in stage (a) and/or (c) with a cooling means such as a cooling jacket. Especially preferably, at least two reactors are employed in stage (a) which are connected in parallel and can be operated alternately. In case the reactors are operated in upflow mode, the two or more reactors connected in parallel in stage (a) are particularly preferably tube reactors, multi-tube reactors or multi-plate reactors, more preferably multi-tube reactors and especially preferably shell-and-tube reactors comprising a multitude of tubes such as from 1 to 20 000, preferably from 10 to 10 000, more preferably from 100 to 8000, more preferably from 1000 to 7000 and particularly preferably from 3000 to 6000, tubes. To regenerate the catalyst used for the epoxidation reaction, it is possible for at least one of the reactors connected in parallel to be taken out of operation for the respective reaction stage and the catalyst present in this reactor to be regenerated, with at least one reactor always being available for reaction of the starting material or starting materials in every stage during the course of the continuous process.

As cooling medium used for cooling the reaction media in above-mentioned reactors equipped with cooling jackets, there are no specific restrictions. Especially preferred are oils, alcohols, liquid salts or water, such as river water, brackish water and/or sea water, which can in each case, for example, preferably be taken from a river and/or lake and/or sea close to the chemical plant in which the reactor of the invention and the process of the invention are used and, after any necessary suitable removal of suspended material by filtration and/or sedimentation, be used directly without further treatment for cooling the reactors. Secondary cooling water which is preferably conveyed around a closed circuit is particularly useful for cooling purposes. This secondary cooling water is generally essentially deionized or demineralised water to which at least one antifouling agent has preferably been added. More preferably, this secondary cooling water circulates between the reactor of the invention and, for example, a cooling tower. Preference is likewise given to the secondary cooling water being, for example, countercooled in at least one countercurrent heat exchanger by, for example, river water, brackish water and/or sea water.

In stage (c), particular preference is given to using a shaft reactor, more preferably a continuously operated shaft reactor and particularly preferably a continuously operated, adiabatic shaft reactor.

Therefore, the present invention also relates to a process as described above wherein in stage (a), at least two shell-and-tube reactors each having of from 1 to 20.000 internal tubes and being continuously operated in upflow mode, said reactors being operated in parallel, are employed, and wherein in stage (c), an adiabatic shaft reactor being being continuously operated in upflow mode, is employed. Still more preferably, the reaction in at least one of these reactors, more preferably in the at least two reactors of stage (a) and still more preferably in all reactors used in states (a) and (c) is conducted such that in the respective reactor, a single liquid phase is present.

The hydrogen peroxide is used in the process according to the invention in the form of an aqueous solution with a hydrogen peroxide content of generally of from 1 to 90 wt.-%, preferably of from 10 to 70 wt.-%., more preferably from 10 to 60 wt.-%. A solution having of from 20 to less than 50 wt.-% of hydrogen peroxide is particularly preferred.

According to another embodiment of the present invention, a crude aqueous hydrogen peroxide solution can be employed. As crude aqueous hydrogen peroxide solution, a solution can be used which is obtained by extraction of a mixture with essentially pure water wherein the mixture results from a process known as anthrachinone process (see, e.g., Ullmann's Encyclopedia of Industrial Chemistry, 5th edition, volume 3 (1989) pages 447-457). In this process, the hydrogen peroxide formed is generally separated by extraction from the working solution. This extraction can be performed with essentially pure water, and the crude aqueous hydrogen peroxide is obtained. According to one embodiment of the present invention, this crude solution can be employed without further purification. The production of such a crude solution is described, for example, in European patent application EP 1 122 249 A1. As to the term "essentially pure water", reference is made to paragraph 10, page 3 of EP 1 122 249 A1 which is incorporated by reference.

To prepare the hydrogen peroxide which is preferably used, it is possible to employ, for example, the anthraquinone process by means of which virtually the entire world production of hydrogen peroxide is produced. An overview of the anthraquinone process is given in "Ullmann's Encyclopedia of Industrial Chemistry", 5th edition, volume 13, pages 447 to 456.

It is likewise conceivable to obtain hydrogen peroxide by converting sulfuric acid into peroxodisulfuric acid by anodic oxidation with simultaneous evolution of hydrogen at the cathode. Hydrolysis of the peroxodisulfuric acid then leads via peroxomonosulfuric acid to hydrogen peroxide and sulfuric acid which is thus obtained back.

Of course, the preparation of hydrogen peroxide from the elements is also possible.

Before hydrogen peroxide is used in the process of the invention, it is possible to free, for example, a commercially available hydrogen peroxide solution of undesirable ions. Conceivable methods are, inter alia, those described, for example, in U.S. Pat. No. 5,932,187, DE 42 22 109 A1 or U.S. Pat. No. 5,397,475. It is likewise possible to remove at least one salt present in the hydrogen peroxide solution from the hydrogen peroxide solution by means of ion exchange in an apparatus which contains at least one nonacidic ion exchanger bed having a flow cross-sectional area F and a height H which are such that the height H of the ion exchanger bed is less than or equal to $2.5 \cdot F^{1/2}$, in particular less than or equal to $1.5 \cdot F^{1/2}$. For the purposes of the present invention, it is in principle possible to use all nonacidic ion exchanger beds comprising cation exchangers and/or anion exchangers. It is also possible for cation and anion exchangers to be used as mixed beds within one ion exchanger bed. In a preferred embodiment of the present invention, only one type of nonacidic ion exchangers is used. Further preference is given to the use of basic ion exchange, particularly preferably that of a basic anion exchanger and more particularly preferably that of a weakly basic anion exchanger.

The pressure in the reactors is generally in the range of from 10 to 30 bar, more preferably from 15 to 25 bar. The temperature of the cooling water is in the range of preferably from 20 to 70° C., more preferably from 25 to 65° C. and particularly preferably from 30 to 60° C.

According to the preferred embodiment of the invention according to which the reactor or the reactors in stage (a) are fixed-bed reactors, the product mixture obtained therefrom essentially consists of propylene oxide, unreacted propylene, methanol, water, and hydrogen peroxide.

According to a preferred embodiment, the product mixture obtained from stage (a) has a methanol content in the range of from 55 to 75 wt.-%, especially preferably of from 60 to 70 wt.-%, based on the total weight of the product mixture, a water content in the range of from 5 to 25 wt.-%, especially preferably of from 10 to 20 wt.-%, based on the total weight of the product mixture, a propylene oxide content in the range of from 5 to 20 wt.-%, especially preferably of from 8 to 15 wt.-%, based on the total weight of the product mixture, and a propylene content in the range of from 1 to 10 wt.-%, especially preferably of from 1 to 5 wt.-%, based on the total weight of the product mixture.

The temperature of the product mixture obtained from stage (a) is preferably in the range of from 40 to 60° C., more preferably of from 45 to 55° C. Prior to being fed to the distillation column of (b), the product mixture is preferably heated up in at least one heat exchanger to a temperature in the range of from 50 to 80° C., more preferably of from 60 to 70° C.

According to an object of the present invention, heating up the product stream obtained from stage (a) is carried out using, at least partially, the bottoms stream of the distillation column of stage (b). Thus, heat integration of the overall epoxidation process is still further improved. According to a preferred embodiment, of from 50 to 100%, more preferably of from 80 to 100% and especially preferably of from 90 to 100% of the bottoms stream obtained from the distillation column used in (b) are used for heating up the product stream obtained from (a) from a temperature in the range of from 45 to 55° C. to a temperature in the range of from 65 to 70° C.

According to stage (b), unreacted propylene is separated from the mixture resulting from stage (a). This separation is carried out by distillation using at least one distillation column. The reaction mixture obtained from the at least one reactor, preferably from the at least two reactors used in stage (a), comprising unreacted propylene, propylene oxide, methanol, water and unreacted hydrogen peroxide, is introduced in the distillation column. The distillation column is preferably operated at a top pressure of from 1 to 10 bar, more preferably of from 1 to 5 bar, more preferably of from 1 to 3 bar and still more preferably of from 1 to 2 bar such as 1, 1.1, 1.2, 1.3, 1.4, 1.5, 1.6, 1.7, 1.8, 1.9 or 2 bar. According to an especially preferred embodiment, the distillation column has from 5 to 60, preferably from 10 to 50 and especially preferably from 15 to 40 theoretical stages.

According to a still further preferred embodiment, the reaction mixture obtained from (a) is fed to the distillation column of (b) from 2 to 30 theoretical stages below the top, preferably from 10 to 20 theoretical stages below the top of the column.

At the top of the distillation column of (b), a stream essentially consisting of propylene oxide, methanol and unreacted propene is obtained. At the top of the column, a mixture is obtained having a water content of not more than 0.5 wt.-%, preferably of not more than 0.4 wt.-% and still more preferably of not more than 0.3 wt.-%, and having a hydrogen peroxide content of not more than 100 ppm, preferably of not more than 20 ppm and still more preferably of not more than 10 ppm, in each case based on the total weight of the mixture obtained at the top of the column.

At the bottom of the distillation column, a stream essentially consisting of methanol, water and unreacted hydrogen peroxide is obtained. At the bottom of the column, a mixture is obtained having a propene content of not more than 50 ppm, preferably of not more than 10 ppm and still more preferably of not more than 5 ppm, and having a propylene oxide content of not more than 50 ppm, preferably of not more than 20 ppm and still more preferably of not more than 10 ppm, in each case based on the total weight of the mixture obtained at the bottom of the column.

According to a still further preferred embodiment, the distillation column used in (b) is configured as dividing wall column having at least one side-offtake, preferably one side-offtake. Preferably, the dividing wall column preferably has from 20 to 60, more preferably from 30 to 50 theoretical stages.

The upper combined region of the inflow and offtake part of the dividing wall column preferably has from 5 to 50%, more preferably from 15 to 30%, of the total number of theoretical stages in the column, the enrichment section of the inflow part preferably has from 5 to 50%, more preferably from 15 to 30%, the stripping section of the inflow part preferably has from 15 to 70%, more preferably from 20 to 60%, the stripping section of the offtake part preferably has from 5 to 50%, more preferably from 15 to 30%, the enrichment section of the offtake part preferably has from 15 to 70%, more preferably from 20 to 60%, and the lower combined region of the inflow and offtake part of the column preferably has from 5 to 50%, more preferably from 15 to 30%, in each case of the total number of theoretical stages in the column.

It is likewise advantageous for the inlet via which the product mixture obtained from (a) is fed into the column and the side offtake via which the a part of the methanol, preferably of from 0 to 50%, more preferably of from 1 to 40%, still more preferably of from 5 to 30% and especially preferably of from 10 to 25% of the methanol, is taken off as intermediate boiler and, still more preferably, directly fed back to stage (a), to be arranged at different heights in the column relative to the position of the theoretical stages. The inlet is preferably located at a position which is from 1 to 25, more preferably from 5 to 15 theoretical stages above or below the side offtake.

The dividing wall column used in the process of the present invention is preferably configured either as a packed column containing random packing or ordered packing or as a tray column. For example, it is possible to use sheet metal or mesh packing having a specific surface area of from 100 to 1000 $m^2/m^3$, preferably from about 250 to 750 $m^2/m^3$, as ordered packing. Such packing provides a high separation efficiency combined with a low pressure drop per theoretical stage.

In the abovementioned configuration of the column, the region of the column divided by the dividing wall, which consists of the enrichment section of the inflow part, the stripping section of the offtake part, the stripping section of the inflow part and the enrichment section of the offtake part, or parts thereof is/are provided with ordered packing or random packing. The dividing wall can be thermally insulated in these regions.

The differential pressure over the dividing wall column can be utilized as regulating parameter for the heating power. The distillation is advantageously carried out at a pressure at the top of from 1 to 10 bar, preferably from 1 to 5 bar, more preferably from 1 to 3 bar and still more preferably of from 1 to 2 bar such as 1, 1.1, 1.2, 1.3, 1.4, 1.5, 1.6, 1.7, 1.8, 1.9 or 2 bar.

The distillation is preferably carried out in a temperature range from 65 to 100° C., more preferably from 70 to 85° C. The distillation temperature is measured at the bottom of the tower.

In case such a divided wall column is used, at the top of the distillation column of (b), a stream essentially consisting of propylene oxide, methanol and unreacted propylene is obtained. At the top of the column, a mixture is obtained having a water content of not more than 500 ppm, preferably of not more than 400 ppm, and still more preferably of not more than 300 ppm, and having a hydrogen peroxide content of not more than 50 ppm, preferably of not more than 20 ppm and still more preferably of not more than 10 ppm, in each case based on the total weight of the mixture obtained at the top of the column. Furthermore, the top stream obtained has a propylene content of from 15 to 35 wt.-%, preferably of from 20 to 30 wt.-% and still more preferably of from 20 to 25 wt.-%, a propylene oxide content of from 50 to 80 wt.-%, preferably of from 55 to 75 wt.-% and especially preferably of from 60 to 70 wt.-%, and a methanol content of from 5 to 20 wt.-%, more preferably of from 7.5 to 17.5 wt.-% and especially preferably of from 10 to 15 wt.-%, in each case based on the total weight of the top stream.

At the side-offtake of the distillation column, a stream essentially consisting of methanol and water is obtained. At the side-offtake of the column, a mixture is obtained having a methanol content of at least 95 wt.-%, preferably at least 96 wt.-% and still more preferably at least 97 wt.-%, and having a water content of not more than 5 wt.-%, preferably of not more than 3.5 wt.-% and still more preferably of not more than 2 wt.-%, in each case based on the total weight of the mixture obtained at the side-offtake of the column.

At the bottom of the distillation column, a stream essentially consisting of methanol, water and unreacted hydrogen peroxide is obtained. At the bottom of the column, a mixture is obtained having propene content of not more than 50 ppm, preferably of not more than 10 ppm and still more preferably of not more than 5 ppm, and having a propylene oxide content of not more than 50 ppm, preferably of not more than 20 ppm and still more preferably of not more than 10 ppm, in each case based on the total weight of the mixture obtained at the bottom of the column.

At least part of the stream taken from the side of the dividing wall column can be recycled as solvent into stage (a) of the inventive process. Preferably, at least 90%, more preferably at least 95% of the stream taken from the side-offtake are recycled into stage (i).

The bottoms stream taken from the of the distillation column, preferably the dividing wall distillation column, essentially consisting of methanol, water and unreacted hydrogen peroxide, is then fed to the reactor of stage (c). Preferably, the bottoms stream is cooled prior to being introduced into the reactor via, for example, one-stage cooling or two-stage cooling, more preferably to a temperature of from 20 to 40° C., still more preferably to a temperature of from 30 to 40° C. Still more preferably, fresh propene, is additionally added directly in to the reactor of stage (c) or added to the bottoms stream obtained from (b) prior to introducing same into the reactor of stage (c). Alternatively or additionally, fresh hydrogen peroxide can be added.

The selectivity of the overall process with stages (a) to (c) in respect of hydrogen peroxide is preferably in the range from 78 to 99%, more preferably in the range from 88 to 97% and particularly preferably in the range from 90 to 96%.

The total hydrogen peroxide conversion is preferably at least 99.5%, more preferably at least 99.6%, more preferably at least 99.7% and particularly preferably at least 99.8%.

The reaction mixture obtained from stage (c) preferably has a methanol content of from 50 to 90 wt.-%, more preferably of from 60 to 85 wt.-% and especially preferably of from 70 to 80 wt.-%, based on the total weight of the reaction mixture. The water content is preferably in the range of from 5 to 45 wt.-%, more preferably of from 10 to 35 wt.-% and especially preferably of from 15 to 25 wt.-%, based on the total weight of the reaction mixture. The propylene oxide content is preferably in the range of from 1 to 5 wt.-%, more preferably of from 1 to 4 wt.-% and especially preferably of from 1 to 3 wt.-%, based on the total weight of the reaction mixture. The propylene content is preferably in the range of from 0 to 5 wt.-%, more preferably of from 0 to 3 wt.-% and especially preferably of from 0 to 1 wt.-%, based on the total weight of the reaction mixture.

The product mixture taken from the reactor of stage (c) can be fed to further down-stream stages where high-purity propylene oxide is suitably separated from said product mixture. Additionally, the stream taken from the top of the distillation column of stage (b) ca be combined with the product mixture taken from the reactor of stage (c) which is then fed to said downstream purification stages. Alternatively, it is possible to separately feed the product mixture taken from the reactor of stage (c) and the top stream of the distillation column of stage (b) to said downstream purification stages.

In the context of the present invention, it has been surprisingly found that the selectivity of the catalyst and the catalyst obtainable or obtained by the process according to the invention, respectively, shows improved catalytic properties in hydrocarbon conversion processes compared to catalysts of the same composition which have not been contacted with a hydrocarbon in accordance with (ii) of the invention. Improved catalytic properties means that the catalyst show longer life time and/or higher selectivity concerning the valuable product and/or lower selectivities concerning by-products and/or secondary products and/or improved activity. Typically, with the pretreated catalyst of the invention, in particular the catalyst as described above having the carbonaceous material deposited thereon in an amount of from 0.01 to 0.06 wt.-%, more preferably from 0.02 to 0.05 wt.-% and even more preferably from 0.03 to 0.04 wt.-%, improved selectivities for epoxidation reaction by-products and secondary products can be achieved. In particular, this is achieved for TS-1 zeolite containing catalysts employed for the epoxidation of propylene with hydrogen peroxide, in particular in the presence of methanol or a methanol/water mixture as solvent, where a high selectivity for propylene oxide, based on hydrogen peroxide is achieved for a long period of time wherein, at the same time, low selectivities for by-products and secondary products such as methoxypropanols, oxygen, and hydroperoxides are obtained.

The present invention includes the following embodiments, including the specific combinations of these embodiments as indicated by the respective dependencies defined therein.

1. A process for the preparation of a catalyst for the use in a hydrocarbon conversion reaction, said catalyst containing a titanium zeolite and carbonaceous material, the catalyst containing said carbonaceous material in an amount of from 0.01 to 0.5% by weight based on the total weight of titanium zeolite contained in the catalyst, the process comprising
   (i) preparing a catalyst containing the titanium zeolite;
   (ii) depositing carbonaceous material on the catalyst according to (i) in an amount of from 0.01 to 0.5% by weight based on the total weight of titanium zeolite contained in the catalyst by contacting said catalyst, prior to using the catalyst in said hydrocarbon conversion reaction, with a fluid containing at least one hydrocarbon in an inert atmosphere, to obtain the carbonaceous material containing catalyst,
   wherein in (ii), the catalyst is not contacted with an oxygen containing gas.
2. The process of embodiment 1, wherein in (ii), the fluid is a gas stream.
3. The process of embodiment 1 or 2, wherein the inert atmosphere is an inert gas or a mixture of inert gases, the inert atmosphere preferably being nitrogen.
4. The process of any of embodiments 1 to 3, wherein in (ii), the fluid is a gas stream containing the at least one hydrocarbon and an inert gas or a mixture of inert gases, wherein in the gas stream, the volume ratio of hydrocarbon to inert gas or inert gases is in the range of from 1:50 to 1:5.
5. The process of any of embodiments 1 to 4, wherein the at least one hydrocarbon employed in (i) corresponds to the hydrocarbon being converted in the hydrocarbon conversion process.
6. The process of any of embodiments 1 to 5, wherein the hydrocarbon is an olefin, preferably propylene.
7. The process of any of embodiments 1 to 6, wherein contacting according to (ii) is carried out at a temperature in the range of from 400 to 500° C.
8. The process of any of embodiments 1 to 7, wherein contacting according to (ii) is carried out for a time in the range of from 12 to 48 h.
9. The process of any of embodiments 1 to 8, wherein the titanium zeolite has an MFI, MEL, MWW, BEA or FER structure or a mixed structure of two or more thereof, preferably an MFI structure.
10. The process of any of embodiments 1 to 9, wherein neither before nor after (ii), the catalyst is subject to a silylation treatment.
11. The process of any of embodiments 1 to 10, wherein after (i) and prior to (ii), the catalyst is subject to hydrothermal treatment, the hydrothermal treatment preferably comprising
   (I) treating the catalyst with water in an autoclave, preferably at a pressure of from 2 to 3 bar, preferably at a temperature in the range of from 130 to 150° C., preferably for a period of from 12 to 48 h;
   (II) drying the catalyst, preferably at a temperature in the range of from 100 to 150° C.; and
   (III) calcining the dried catalyst, preferably at a temperature in the range of from 450 to 500° C.

12. The process of any of embodiments 1 to 11, wherein in (i), the titanium zeolite is shaped, preferably extruded, to give a molding comprising the titanium zeolite and preferably at least one binder, in particular a silica binder.
13. The process of any of embodiments 1 to 12, wherein the catalyst contains the carbonaceous material in an amount of from 0.01 to 0.1% by weight, preferably from 0.01 to 0.06% by weight, more preferably from 0.02 to 0.05% by weight, more preferably from 0.03 to 0.04%, based on the total weight of titanium zeolite contained in the catalyst, and wherein in (ii), the carbonaceous material is deposited on the catalyst according to (i) in an amount of from 0.01 to 0.1% by weight, preferably from 0.01 to 0.06% by weight, more preferably from 0.02 to 0.05% by weight, more preferably from 0.03 to 0.04% by weight, based on the total weight of titanium zeolite contained in the catalyst.
14. A catalyst containing a titanium zeolite and carbonaceous material, the catalyst containing the carbonaceous material in an amount of from 0.01 to 0.5%, preferably from 0.01 to 0.1% by weight, more preferably from 0.01 to 0.06% by weight, more preferably from 0.02 to 0.05% by weight, more preferably from 0.03 to 0.04% by weight, based on the total weight of titanium zeolite contained in the catalyst, said catalyst being obtainable or obtained by a process according to any of embodiments 1 to 13, wherein the titanium zeolite has an MFI, MEL, MWW, BEA or FER structure or a mixed structure of two or more thereof, preferably an MFI structure.
15. The catalyst of embodiment 14 insofar as embodiment 14 is dependent on embodiment 12, wherein the molding comprises micropores and mesopores.
16. The catalyst of embodiment 15, wherein the molding comprises the titanium zeolite and the carbonaceous material in an amount of from 70 to 80% by weight, and from 20 to 30% by weight of a binder, preferably a silica binder, in each case based on the total weight of the molding.
17. The catalyst of embodiment 15 or 16, wherein the molding has a crush strength of at least 22 N, preferably from 22 to 25 N, determined using an apparatus from Zwick, type BZ2.5/TS1S as described in detail the specification.
18. Use of a catalyst according to any of embodiments or the 14 to 17 in a process for the conversion of a hydrocarbon, preferably for the oxidation of a hydrocarbon, more preferably for the epoxidation of an olefin, in particular for the epoxidation of propylene.
19. The use of embodiment 18, wherein the process for the conversion of a hydrocarbon is a process for the preparation of propylene oxide in the presence of a catalyst containing at least one titanium zeolite and carbonaceous material, the catalyst comprising said carbonaceous material in a range of from 0.01 to 0.5% by weight based on the total weight of titanium zeolite, the process comprising
   (i) providing a catalyst containing the titanium zeolite;
   (ii) depositing carbonaceous material on the catalyst according to (i) in the range of from 0.01 to 0.5% by weight based on the total weight of titanium zeolite contained in the catalyst by contacting said catalyst, prior to using the catalyst in said hydrocarbon conversion reaction, with a fluid containing at least one hydrocarbon in an inert atmosphere, to obtain the carbonaceous material containing catalyst,
   (iii) contacting the catalyst obtained according to (ii) with a reaction mixture comprising propylene, hydroperoxide, and at least one solvent,
   wherein in (ii), the catalyst is not contacted with an oxygen containing gas.
20. The use of embodiment 19, wherein in (iii), the catalyst is a titanium silicalite-1 catalyst, the hydroperoxide is hydrogen peroxide and the solvent is methanol.
21. The use of embodiment 19 or 20, wherein the catalyst contains the carbonaceous material in an amount of from 0.01 to 0.1% by weight, preferably from 0.01 to 0.06% by weight, more preferably from 0.02 to 0.05% by weight, more preferably from 0.03 to 0.04%, based on the total weight of titanium zeolite contained in the catalyst, and wherein in (ii), the carbonaceous material is deposited on the catalyst according to (i) in an amount of from 0.01 to 0.1% by weight, preferably from 0.01 to 0.06% by weight, more preferably from 0.02 to 0.05% by weight, more preferably from 0.03 to 0.04% by weight, based on the total weight of titanium zeolite contained in the catalyst.

To illustrate the nature and advantageous of the present invention further, the following examples are provided. However, it should be noted that the examples are provided for illustrative purposes only and not to limit the invention. However, they clearly demonstrate that a catalyst prepared by the process of invention shows excellent selectivity characteristics as already described above, and also improved cutting strengths.

EXAMPLES

1. Preparation of the TS-1 Catalyst
Powder Synthesis
Starting Materials:

| | |
|---|---|
| 720 kg | tetraethoxysilane (TEOS) |
| 400 kg | tetrapropylammoniumhydroxide (TPAOH) (40 wt.-% in water) |
| 16 kg | tetraethoxytitane (TEOT) |
| 550 kg | DI water |

In a reaction vessel, 550 kg DI water were provided and stirred. 400 kg TPAOH were added under stirring. Stirring was continued for 1 h. The resulting mixture was transferred in a suitable vessel. The reaction vessel was washed twice with 2000 l DI water in total. In the washed reaction vessel, 300 kg TEOS were provided and stirred. A mixture of 80 kg TEOS and 16 kg TEOT was added to the 300 kg TEOS. The remaining 340 kg TEOS were added. Subsequently, the TPAOH solution was added, and the resulting mixture was stirred for another hour. Then, the reaction vessel was heated and the ethanol obtained was separated by distillation. When the internal temperature of the vessel had reached 95° C., the reaction vessel was cooled. 1143 kg water were added to the resulting suspension in the vessel, and the mixture was stirred for another hour. Crystallization was performed at 175° C. within 24 h at autogenous pressure. The obtained titanium silicalite-1 crystals were separated, dried, and calcined at a temperature of 500° C. in air.

Shaping

TS-1 powder and Walocel were mixed a muller and mixed for 5 min. Within 10 min, the polystyrene dispersion was continuously added. Subsequently, 15 l Ludox were continuously added. The resulting mixture was mixed for 5 min, and PEO was continuously added within 15 min, followed by mixing for 10 min. Then, the water was added. The formable mass was extruded through a matrix having circular holes with a diameter of 1.5 mm. The obtained strands were dried in a band drier at a temperature of 120° C. for 2 h and calcined at a temperature of 550° C. in lean air (100 m$^3$/h air/100 m$^3$/h nitrogen). The yield was 89 kg (extrudates I).

This procedure was repeated, and the yield was 88 kg (extrudates II).

Water Treatment

Starting Materials

| (a) | 88 kg | extrudates I |
|---|---|---|
|  | 890 kg | DI water |
| (b) | 87 kg | extrudates II |
|  | 880 kg | DI water |

For (a), the water was filled in a respective stirred vessel, and the extrudates I were added. At a pressure of 84 mbar, the vessel was heated to a internal temperature of from 139 to 143° C. The resulting pressure was in the range of from 2.1 to 2.5 bar. Water treatment was carried out for 36 h. The extrudates were separated by filtration, dried for 16 h at 123° C. in air, heated to a temperature of 470° C. with 2° C./min and kept at a temperature of 490° C. in air for 5 h. The yield was 81.2 kg.

For (b), the water was filled in a respective stirred vessel, and the extrudates II were added. At a pressure of 84 mbar, the vessel was heated to a internal temperature of from 141 to 143° C. The resulting pressure was in the range of from 2.3 to 2.5 bar. Water treatment was carried out for 36 h. The extrudates were separated by filtration, dried for 16 h at 123° C. in air, heated to a temperature of 470° C. with 2° C./min and kept at a temperature of 490° C. in air for 5 h. The yield was 77.3 kg.

2. Depositing Carbonaceous Material on the Catalyst Extrudates (b)

2.1 180 g of catalyst extrudates (b) were filled in a vertical reactor. At the bottom, the reactor contained 18 g steatite pellets having a diameter of 2-3 mm. At the top, the reactor contained 17 g steatite pellets having a diameter of 5 mm. The reactor was heated stepwise to a temperature of 450° C. with nitrogen having a flow rate of 600 Nl/h (norm liter per hour). This temperature was maintained. Then, propene was passed through the reactor for 16 h with a flow rate of 20 Nl/h. Subsequently, the catalyst is cooled under nitrogen and removed from the reactor at ambient temperature. Yield: 180 g. The grey strands were manually separated from the obtained extrudates. Yield of grey strands: 24 g.

2.2 176 g of catalyst extrudates (b) were filled in a vertical reactor. At the bottom, the reactor contained 18 g steatite pellets having a diameter of 2-3 mm. At the top, the reactor contained 21 g steatite pellets having a diameter of 5 mm. The reactor was heated stepwise to a temperature of 450° C. with nitrogen having a flow rate of 600 Nl/h (norm liter per hour). This temperature was maintained. Then, propene was passed through the reactor for 30 h with a flow rate of 30 Nl/h. Subsequently, the catalyst is cooled under nitrogen and removed from the reactor at ambient temperature. Yield: 176 g. The grey strands were manually separated from the obtained extrudates. Yield of grey strands: 31 g.

2.3 175 g of catalyst extrudates (b) were filled in a vertical reactor. At the bottom, the reactor contained 18 g steatite pellets having a diameter of 2-3 mm. At the top, the reactor contained 24 g steatite pellets having a diameter of 5 mm. The reactor was heated stepwise to a temperature of 450° C. with nitrogen having a flow rate of 600 Nl/h (norm liter per hour). This temperature was maintained. Then, propene was passed through the reactor for 12 h with a flow rate of 39 Nl/h. Subsequently, the catalyst is cooled under nitrogen and removed from the reactor at ambient temperature. Yield: 175 g. The grey strands were manually separated from the obtained extrudates. Yield of grey strands: 20 g.

2.4 177 g of catalyst extrudates (b) were filled in a vertical reactor. At the bottom, the reactor contained 18 g steatite pellets having a diameter of 2-3 mm. At the top, the reactor contained 19 g steatite pellets having a diameter of 5 mm. The reactor was heated stepwise to a temperature of 450° C. with nitrogen having a flow rate of 750 Nl/h (norm liter per hour). This temperature was maintained. Then, propene was passed through the reactor for 21 h with a flow rate of 35 Nl/h. Subsequently, the catalyst is cooled under nitrogen and removed from the reactor at ambient temperature. Yield: 177 g. The grey strands were manually separated from the obtained extrudates. Yield of grey strands: 47 g.

2.5 179 g of catalyst extrudates (b) were filled in a vertical reactor. At the bottom, the reactor contained 19 g steatite pellets having a diameter of 2-3 mm. At the top, the reactor contained 26 g steatite pellets having a diameter of 5 mm. The reactor was heated stepwise to a temperature of 450° C. with nitrogen having a flow rate of 600 Nl/h (norm liter per hour). This temperature was maintained. Then, propene was passed through the reactor for 30 h with a flow rate of 39 Nl/h. Subsequently, the catalyst is cooled under nitrogen and removed from the reactor at ambient temperature. Yield: 179 g. The grey strands were manually separated from the obtained extrudates. Yield of grey strands: 24 g.

2.6 184 g of catalyst extrudates (b) were filled in a vertical reactor. At the bottom, the reactor contained 18 g steatite pellets having a diameter of 2-3 mm. At the top, the reactor contained 28 g steatite pellets having a diameter of 5 mm. The reactor was heated stepwise to a temperature of 450° C. with nitrogen having a flow rate of 600 Nl/h (norm liter per hour). This temperature was maintained. Then, propene was passed through the reactor for 30 h with a flow rate of 70 Nl/h. Subsequently, the catalyst is cooled under nitrogen and removed from the reactor at ambient temperature. Yield: 178 g. The grey strands were manually separated from the obtained extrudates. Yield of grey strands: 16 g.

2.7 The grey strands obtained from 2.1 to 2.6 were mixed, and their total organic carbon content (TOC content) was determined to 0.074% by weight. These strands are referred to as catalyst A1 in the following. The whitish strands, remaining after separation of the grey strands as described in 2.1 to 2.6 above, were also mixed, and their total organic carbon content (TOC content) was determined to 0.031% by weight. These strands are referred to as catalyst A2 in the following. The strands (extrudates (b)) obtained after water treatment as described in 1. above are referred to as catalyst C in the following.

3. Epoxidation Test

The catalysts A1 (inventive), A2 (inventive), and C (comparative) were employed as catalysts for the epoxidation of propylene with hydrogen peroxide in methanol as solvent.

As reactor, a vertically arranged tube reactor with a length of 1400 mm and an outer diameter of 10 mm, internal diameter 7 mm, was used. The reactor was equipped with a cooling jacket. The reactor was filled with 15 g of the respective catalysts. Through the reactor, the starting materials were passed with the following flow rates: methanol (49 g/h); hydrogen peroxide (9 g/h); propylene (7 g/h). Via the cooling medium passed through the cooling jacket, the temperature of the reaction mixture was adjusted so that the hydrogen peroxide conversion, determined on the basis of the reaction mixture leaving the reactor, was essentially constant at 90%. This temperature, after induction periods of typically 50 to 100 h, was in the range of from 35 to 45° C. The pressure within the reactor was held constant at 20 bar, and the reaction mixture—apart from the fixed-bed catalyst—consisted of one single liquid phase.

As hydrogen peroxide solution, an aqueous hydrogen peroxide solution (stabilized, 40 wt.-% of hydrogen peroxide) was employed. As stabilizing agents, this hydrogen peroxide stream contained 111 micromol sodium ions per 1 mol hydrogen peroxide, 91.8 micromol sodium phosphorus (P) per 1 mol hydrogen peroxide, and 80 mg nitrate per kg of hydrogen peroxide. Apart from sodium, the hydrogen peroxide stream contained only traces (less than 10 wt.-ppb) of other metals (iron, aluminum, tin, palladium). Such aqueous hydrogen peroxide solution are commercially available, e.g. from Solvay as aqueous crude washed hydrogen peroxide. As propylene, polymer grade propene (99.9 wt.-% propene) was employed.

The product stream leaving the reactor was decompressed to ambient pressure into a vessel where gas and liquid phases were separated. The amount of gas was determined volumetrically and its composition analyzed by gas chromatography. The total concentration of peroxides was determined iodometrically. The concentration of $H_2O_2$ was determined colorimetrically using the titanyl sulfate method. The difference between the two values is generally a good measure for the concentration of hydroperoxypropanols (1-hydroperoxy-2-propanol and 2-hydroperoxy-1-propanol); this was confirmed by determining the amount of propylene glycol by GC before and after reducing the mixture with excess triphenylphosphine. All other organic components were determined by GC using a FID detector and using 1,4-dioxane as an internal standard. In particular, the selectivity of the epoxidation process with respect to byproducts and secondary products oxygen, methoxypropanols (MOP), and hydroperoxides was determined. Selectivities were calculated as selectivities based on hydrogen peroxide.

The respective values for the epoxidation process after 200 h, 300 h, 400 h, and 500 h, are shown in Table 1 below. It is clearly shown that the preferred catalysts according to the present invention have superior selectivity characteristics compared to the comparative catalyst C which does not contain carbonaceous material. Further, one can see that the amount of carbonaceous material of catalyst A2 which is in the most preferred range of from 0.01 to 0.06 wt.-% is even better than an amount of 0.074 wt.-% (catalyst A1).

Additionally, after a runtime of 300 h, the temperature of the cooling medium passed through the jacket of the tube reactor had to be increased to 42° C. for catalyst C in order to allow for a hydrogen peroxide conversion of 90% which, as indicated above, was chosen as internal standard allowing for a comparison of the 3 catalysts. As far as the inventive catalysts are concerned, the respective temperature, after 400 h, was 40° C. for catalyst A2 and 42° C. for catalyst A1. After 400 h, said temperature was 44° C. for catalyst C, but only 41.5° C. for catalyst A2 and 42° C. for catalyst A2. After 500 h, said temperature was 45° C. for catalyst C, but only 43° C. for both catalysts A1 and A2. Obviously, the inventive catalysts showed improved lifetime characteristics, in particular for long runtime experiments important for industrial-scale processes. Moreover, in addition to the superior selectivity values with regard to by-products and secondary products as shown in Table 1 below, the catalyst A2 was also found to be the best catalyst as far as said temperature-based lifetime characteristics are concerned.

TABLE 1

| | | catalyst A1 | catalyst A2 | catalyst C |
|---|---|---|---|---|
| after # h | selectivity of # (based on $H_2O_2$) | selectivities/% (at $H_2O_2$ conversion = 90 ± 2%) | | |
| 200 | propylene oxide | 95.5 | 96.3 | 95.7 |
| | oxygen | 0.5 | 0.3 | 0.4 |
| | hydroperoxides | 1.4 | 1.5 | 1.5 |
| | methoxypropanols | 2.3 | 1.7 | 2.3 |
| 300 | propylene oxide | 95.3 | 96.5 | 95.3 |
| | oxygen | 0.6 | 0.3 | 0.5 |
| | hydroperoxides | 1.5 | 1.5 | 1.6 |
| | methoxypropanols | 2.3 | 1.5 | 2.4 |
| 400 | propylene oxide | 94.7 | 95.3 | 94.9 |
| | oxygen | 0.6 | 0.6 | 0.5 |
| | hydroperoxides | 1.7 | 1.7 | 1.7 |
| | methoxypropanols | 2.8 | 2.0 | 2.5 |
| 500 | propylene oxide | 94.9 | 95.7 | 94.9 |
| | oxygen | 0.7 | 0.5 | 0.5 |
| | hydroperoxides | 1.7 | 1.6 | 1.6 |
| | methoxypropanols | 2.6 | 2.0 | 2.6 |

Selectivities (propylene oxide, by-products, secondary products)

The catalysts A1 and A2 have a crush strength determined using a Zwick apparatus as described in detail hereinabove of more slightly more than 23 N. However, catalyst C had a cutting strength of 20.8 N.

The invention claimed is:

1. A process for the preparation of a catalyst for the use in a hydrocarbon conversion reaction,
   the catalyst comprising:
   a titanium zeolite; and
   a carbonaceous material in an amount of from 0.01 to 0.5% by weight based on a total weight of the titanium zeolite in the catalyst;
   the process comprising:
   (i) preparing a catalyst containing the titanium zeolite;
   (ii) treating the catalyst with an inert gas to place the catalyst in an inert atmosphere;
   (iii) elevating the temperature of the catalyst in the inert atmosphere to a temperature above 300° C.; and
   (iv) contacting the catalyst with a fluid comprising a hydrocarbon in the inert atmosphere to deposit a carbonaceous material on the catalyst at the temperature above 300° C. in an amount of from 0.01 to 0.5% by weight based on the total weight of titanium zeolite to obtain the prepared catalyst;
   wherein in (ii-iv), the catalyst is not contacted with an oxygen containing gas; and after the deposition of the carbonaceous material (iv), the catalyst is not subjected to an additional heat treating step.

2. The process of claim 1, wherein the fluid comprising a hydrocarbon is a gas stream.

3. The process of claim 1, wherein the inert gas is nitrogen.

4. The process of claim 1, wherein in (iv), the fluid comprising a hydrocarbon is a gas stream further comprising an inert gas or a mixture of inert gases, wherein in the gas stream, a volume ratio of hydrocarbon to inert gas or inert gases is in the range of from 1:50 to 1:5.

5. The process of claim 1, wherein the hydrocarbon contacting the catalyst is the hydrocarbon being converted in the hydrocarbon conversion process.

6. The process of claim 1, wherein the hydrocarbon contacting the catalyst is an olefin.

7. The process of claim 1, wherein the hydrocarbon contacting the catalyst is propylene.

8. The process of claim 1, wherein the temperature of contacting the catalyst with the fluid comprising a hydrocarbon is from 400 to 500° C.

9. The process of claim 1, wherein a time of contacting the catalyst with the hydrocarbon is from 12 to 48 h.

10. The process of claim 1, wherein the titanium zeolite has an MFI, MEL, MWW, BEA or FER structure or a mixed structure of two or more thereof.

11. The process of claim 1, wherein the titanium zeolite has an MFI structure.

12. The process of claim 1, wherein the catalyst is not subject to a silylation treatment.

13. The process of claim 1, further comprising hydrothermal treatment of the catalyst containing the titanium zeolite prior to placing the catalyst in an inert atmosphere.

14. The process of claim 1, wherein preparing the catalyst containing the titanium zeolite comprises shaping the catalyst to obtain a molding comprising the titanium zeolite.

15. The process of claim 1, wherein preparing the catalyst containing the titanium zeolite comprises a silica binder and shaping the catalyst to obtain a molding comprising the titanium zeolite and a silica binder.

16. The process of claim 1, wherein the prepared catalyst contains the carbonaceous material in the amount deposited on the catalyst during the contacting of the catalyst with the hydrocarbon in the inert atmosphere.

17. A catalyst obtained by the process of claim 1, comprising a titanium zeolite and carbonaceous material, wherein an amount of the carbonaceous material is from 0.01 to 0.5%, based on the total weight of titanium zeolite in the catalyst, and wherein the titanium zeolite has an MFI, MEL, MWW, BEA or FER structure or a mixed structure of two or more thereof.

18. The catalyst of claim 17, wherein the titanium zeolite has an MFI structure.

19. The catalyst of claim 17, wherein in (i), the catalyst is a shaped molding comprising the titanium zeolite, and and further comprising micropores and mesopores.

20. The catalyst of claim 19, wherein the molding further comprises a silica binder and wherein an amount of the titanium zeolite and the carbonaceous material is from 70 to 80% by weight, and an amount of the silica binder is from 20 to 30% by weight, in each case based on the total weight of the molding.

21. The catalyst of claim 19, wherein a crush strength of the molding is at least 22 N, determined using an apparatus from Zwick, type BZ2.5/TS1S.

22. A method for converting a hydrocarbon comprising contacting the hydrocarbon to be converted with the catalyst to of claim 17.

23. The method of claim 22, wherein the process for the conversion of a hydrocarbon is a process for the preparation of propylene oxide, and the process comprises contacting the catalyst with a reaction mixture comprising propylene, hydroperoxide, and at least one solvent.

24. The method of claim 23, wherein the catalyst is a titanium silicalite-1 catalyst, the hydroperoxide is hydrogen peroxide and the solvent is methanol.

25. The method of claim 23, wherein the prepared catalyst contains the carbonaceous material in the amount deposited on the catalyst during the contacting of the catalyst with the hydrocarbon in the inert atmosphere.

26. The method of claim 22, wherein said hydrocarbon is propylene and the conversion is into propylene oxide.

27. A process for the preparation of a catalyst for the use in a hydrocarbon conversion reaction, the catalyst comprising:
   a titanium zeolite; and
   a carbonaceous material in an amount of from 0.01 to 0.5% by weight based on a total weight of the titanium zeolite in the catalyst;
   the process comprising:
   (i) preparing a catalyst containing the titanium zeolite;
   (ii) treating the catalyst with an inert gas to place the catalyst in an inert atmosphere;
   (iii) elevating the temperature of the catalyst in the inert atmosphere to a temperature above 300° C.; and
   (iv) contacting the catalyst with a fluid containing a hydrocarbon in the inert atmosphere to deposit a carbonaceous material on the catalyst at the temperature above 300° C. in an amount of from 0.01 to 0.5% by weight based on the total weight of titanium zeolite to obtain the prepared catalyst;
   wherein in (ii-iv), the catalyst is not contacted with an oxygen containing gas; and after the deposition of the carbonaceous material (iv), the catalyst is not subjected to an additional heat treating step, and
   wherein the catalyst shows improved catalytic properties in the hydrocarbon conversion processes compared to a catalyst of the same composition which has not been contacted with a hydrocarbon in accordance with (ii-iv).

28. The method of claim 27, wherein said improved catalytic properties result in a longer life time and/or higher selectivity concerning a valuable product and/or lower selectivities concerning a by-product and/or secondary product and/or improved activity.

29. The method of claim 28, wherein said carbonaceous material is deposited on said catalyst in an amount of from 0.01 to 0.06 wt.-%.

30. A catalyst obtained by the method of claim 29.

31. The catalyst of claim 30, which exhibits improved selectivity for propylene oxide in the epoxidation reaction of propylene with hydrogen peroxide in the presence of methanol or a methanol/water mixture as solvent.

* * * * *